(12) United States Patent
Ruthven et al.

(10) Patent No.: US 8,142,617 B2
(45) Date of Patent: *Mar. 27, 2012

(54) APPARATUS AND METHOD FOR DEGRADING A WEB IN THE MACHINE DIRECTION WHILE PRESERVING CROSS-MACHINE DIRECTION STRENGTH

(75) Inventors: Paul J. Ruthven, Neenah, WI (US); Dale T. Gracyalny, Alpharetta, GA (US); Galyn A. Schulz, Greenville, WI (US)

(73) Assignee: Georgia-Pacific Consumer Products LP, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/861,462

(22) Filed: Aug. 23, 2010

(65) Prior Publication Data

US 2011/0042024 A1 Feb. 24, 2011

Related U.S. Application Data

(60) Continuation of application No. 11/611,954, filed on Dec. 18, 2006, now Pat. No. 7,857,941, which is a division of application No. 10/808,431, filed on Mar. 25, 2004, now Pat. No. 7,182,838, which is a division of application No. 10/036,770, filed on Dec. 21, 2001, now Pat. No. 6,733,626.

(51) Int. Cl.
*D21H 27/02* (2006.01)
*B31F 1/07* (2006.01)

(52) U.S. Cl. ........ 162/362; 162/114; 162/117; 428/131; 428/153; 101/23

(58) Field of Classification Search .......... 162/109–117, 162/361, 362, 204, 205; 428/131, 134–137, 428/152–154; 492/20; 101/23, 32

See application file for complete search history.

(56) References Cited

U.S. PATENT DOCUMENTS

| D34,028 S | 2/1901 | Ault |
| 673,041 A | 4/1901 | Ault |
| 1,224,650 A | 5/1917 | Kitchen |

(Continued)

FOREIGN PATENT DOCUMENTS

CA 2053505 4/1999

(Continued)

OTHER PUBLICATIONS

Co-pending U.S. Appl. No. 60/165,080, filed Nov. 12, 1999.

(Continued)

*Primary Examiner* — Eric Hug
(74) *Attorney, Agent, or Firm* — Laura L. Bozek

(57) ABSTRACT

An embossing system for embossing and perforating at least a portion of a web is provided comprising a first embossing roll having embossing elements and at least a second embossing roll having embossing elements, wherein the elements of the first and second embossing rolls define perforate nips for embossing and perforating the web and wherein at least a predominate number of the perforate nips are substantially oriented in the cross-machine direction. Moreover, substantially all of the nips defined by the embossing elements of the first and second embossing rolls can be substantially oriented in the cross-machine direction. Further, the cross-machine embossing elements are at an angle of about 85° to 95° from the machine direction.

23 Claims, 17 Drawing Sheets

U.S. PATENT DOCUMENTS

| | | |
|---|---|---|
| 1,284,517 A | 11/1918 | Whitney |
| 1,384,515 A | 7/1921 | Conradson et al. |
| 2,771,363 A | 11/1956 | Fish |
| 2,803,188 A | 8/1957 | Duvall |
| 2,878,553 A | 3/1959 | Hirsch |
| 3,301,746 A | 1/1967 | Sanford et al. |
| 3,337,388 A | 8/1967 | Wosaba, II |
| 3,432,936 A | 3/1969 | Cole et al. |
| 3,545,705 A | 12/1970 | Hodgson |
| 3,549,742 A | 12/1970 | Benz |
| RE27,201 E | 10/1971 | Mittman |
| RE27,453 E | 8/1972 | Schutte et al. |
| 3,803,936 A | 4/1974 | Kroeper |
| 3,858,623 A | 1/1975 | Lefkowitz |
| 3,905,863 A | 9/1975 | Ayers |
| 3,925,127 A | 12/1975 | Yoshioka |
| 3,940,529 A | 2/1976 | Hepford et al. |
| 3,953,638 A | 4/1976 | Kemp |
| 3,974,025 A | 8/1976 | Ayers |
| 3,994,771 A | 11/1976 | Morgan, Jr. et al. |
| 4,041,989 A | 8/1977 | Johansson et al. |
| 4,071,050 A | 1/1978 | Codorniu |
| 4,102,737 A | 7/1978 | Morton |
| 4,112,982 A | 9/1978 | Bugge et al. |
| 4,125,659 A | 11/1978 | Klowak et al. |
| 4,127,637 A | 11/1978 | Pietreniak et al. |
| 4,149,571 A | 4/1979 | Burroughs |
| 4,157,276 A | 6/1979 | Wandel et al. |
| 4,161,195 A | 7/1979 | Khan |
| 4,182,381 A | 1/1980 | Gisbourne |
| 4,184,519 A | 1/1980 | McDonald et al. |
| 4,280,978 A | 7/1981 | Dannheim et al. |
| 4,314,589 A | 2/1982 | Buchanan et al. |
| 4,320,162 A | 3/1982 | Schulz |
| 4,325,768 A | 4/1982 | Schulz |
| 4,325,773 A | 4/1982 | Schulz |
| 4,326,002 A | 4/1982 | Schulz |
| 4,359,069 A | 11/1982 | Hahn |
| 4,376,455 A | 3/1983 | Hahn |
| 4,376,671 A | 3/1983 | Schulz |
| 4,379,735 A | 4/1983 | MacBean |
| 4,453,573 A | 6/1984 | Thompson |
| 4,469,735 A | 9/1984 | Trokhan |
| 4,529,480 A | 7/1985 | Trokhan |
| 4,543,156 A | 9/1985 | Cheshire et al. |
| 4,564,052 A | 1/1986 | Borel |
| 4,581,087 A * | 4/1986 | Johnson ................ 156/209 |
| 4,592,395 A | 6/1986 | Borel |
| 4,605,585 A | 8/1986 | Johansson |
| 4,611,639 A | 9/1986 | Bugge |
| 4,640,741 A | 2/1987 | Tsuneo |
| 4,671,983 A | 6/1987 | Burt |
| 4,709,732 A | 12/1987 | Kinnunen |
| 4,759,391 A | 7/1988 | Waldvogel et al. |
| 4,759,967 A | 7/1988 | Bauernfeind |
| 4,803,032 A | 2/1989 | Schulz |
| 4,859,519 A | 8/1989 | Cabe, Jr. et al. |
| 4,942,077 A | 7/1990 | Wendt et al. |
| 4,967,085 A | 10/1990 | Bryan et al. |
| 4,998,568 A | 3/1991 | Vöhringer |
| 4,999,235 A | 3/1991 | Lunn et al. |
| 5,016,678 A | 5/1991 | Borel et al. |
| 5,030,500 A | 7/1991 | Perdelwitz, Jr. et al. |
| 5,054,525 A | 10/1991 | Vöhringer |
| 5,066,532 A | 11/1991 | Gaisser |
| 5,085,914 A | 2/1992 | Perdelwitz, Jr. et al. |
| 5,093,068 A | 3/1992 | Schulz |
| 5,098,519 A | 3/1992 | Ramasubramanian et al. |
| 5,103,874 A | 4/1992 | Lee |
| 5,114,777 A | 5/1992 | Gaisser |
| 5,158,521 A | 10/1992 | Singh |
| 5,167,261 A | 12/1992 | Lee |
| 5,199,261 A | 4/1993 | Baker |
| 5,199,467 A | 4/1993 | Lee |
| 5,211,815 A | 5/1993 | Ramasubramanian et al. |
| 5,219,004 A | 6/1993 | Chiu |
| 5,245,025 A | 9/1993 | Trokhan et al. |
| 5,262,007 A | 11/1993 | Van Phan et al. |
| D341,944 S | 12/1993 | Peter |
| 5,277,761 A | 1/1994 | Van Phan et al. |
| 5,320,710 A | 6/1994 | Reeves et al. |
| 5,328,565 A | 7/1994 | Rasch et al. |
| 5,354,425 A | 10/1994 | Mackey et al. |
| 5,379,808 A | 1/1995 | Chiu |
| 5,383,778 A | 1/1995 | Schulz |
| 5,387,385 A | 2/1995 | Murji et al. |
| 5,399,241 A | 3/1995 | Oriaran et al. |
| 5,458,950 A | 10/1995 | Bredenick et al. |
| 5,490,902 A | 2/1996 | Schulz |
| 5,510,002 A | 4/1996 | Hermans et al. |
| 5,543,202 A | 8/1996 | Clark et al. |
| 5,549,790 A | 8/1996 | Van Phan |
| 5,556,509 A | 9/1996 | Trokhan et al. |
| 5,562,805 A | 10/1996 | Kamps et al. |
| D375,844 S | 11/1996 | Edwards et al. |
| 5,607,551 A | 3/1997 | Farrington, Jr. et al. |
| 5,622,734 A | 4/1997 | Clark et al. |
| 5,656,134 A | 8/1997 | Marinack et al. |
| 5,685,954 A | 11/1997 | Marinack et al. |
| 5,690,788 A | 11/1997 | Marinack et al. |
| 5,698,291 A | 12/1997 | Clark et al. |
| 5,702,571 A | 12/1997 | Kamps et al. |
| 5,704,101 A | 1/1998 | Majors et al. |
| 5,776,306 A | 7/1998 | Hepford |
| 5,776,312 A | 7/1998 | Trokhan et al. |
| 5,814,190 A | 9/1998 | Van Phan |
| 5,837,103 A | 11/1998 | Trokhan et al. |
| 5,851,353 A | 12/1998 | Fiscus et al. |
| 5,861,081 A | 1/1999 | Bredendick et al. |
| 5,862,750 A | 1/1999 | Dell'Olmo |
| 5,865,955 A | 2/1999 | Ilvespää et al. |
| 5,885,415 A | 3/1999 | Marinack et al. |
| 5,891,309 A | 4/1999 | Page et al. |
| 5,968,590 A | 10/1999 | Ahonen et al. |
| 6,001,421 A | 12/1999 | Ahonen et al. |
| 6,007,468 A | 12/1999 | Giacometti |
| 6,054,202 A | 4/2000 | Takeuchi et al. |
| 6,080,276 A | 6/2000 | Burgess |
| 6,096,168 A | 8/2000 | Marinack et al. |
| 6,106,928 A | 8/2000 | Laurent et al. |
| 6,119,362 A | 9/2000 | Sundqvist |
| 6,146,496 A | 11/2000 | Phan |
| 6,149,768 A | 11/2000 | Hepford |
| 6,165,298 A * | 12/2000 | Samida et al. ................ 156/73.1 |
| D436,738 S | 1/2001 | Bredendick et al. |
| 6,200,419 B1 | 3/2001 | Phan |
| 6,348,131 B1 | 2/2002 | Kershaw et al. |
| 6,383,958 B1 | 5/2002 | Swanson et al. |
| 6,432,267 B1 | 8/2002 | Watson |
| 6,432,527 B1 | 8/2002 | Perez et al. |
| 6,455,129 B1 | 9/2002 | Kershaw et al. |
| 6,733,626 B2 | 5/2004 | Ruthven et al. |
| 6,887,349 B2 | 5/2005 | Ruthven et al. |
| 6,896,767 B2 | 5/2005 | Wilhelm |
| 7,294,231 B2 * | 11/2007 | Kershaw et al. ............... 162/113 |
| 7,326,322 B2 * | 2/2008 | Ruthven et al. ............... 162/362 |
| 7,857,941 B2 * | 12/2010 | Ruthven et al. ............... 162/114 |
| 2003/0026950 A1 | 2/2003 | Kershaw et al. |
| 2003/0045412 A1 | 3/2003 | Schulz et al. |
| 2003/0106657 A1 | 6/2003 | Baggot |
| 2004/0055694 A1 | 3/2004 | Kershaw et al. |
| 2004/0163783 A1 | 8/2004 | Muller |
| 2004/0200590 A1 | 10/2004 | Wilhelm |
| 2005/0092195 A1 | 5/2005 | Ruthven et al. |

FOREIGN PATENT DOCUMENTS

| | | |
|---|---|---|
| CA | 2 325 682 | 5/2001 |
| CA | 2 325 686 | 5/2001 |
| CA | 2 414 668 | 12/2002 |
| EP | 0 404 189 A1 | 12/1990 |
| EP | 0 495 637 A1 | 7/1992 |
| EP | 0 496 524 | 7/1992 |
| EP | 0 675 225 A2 | 10/1995 |
| EP | 0 707 945 A2 | 4/1996 |
| EP | 0 743 172 | 11/1996 |
| EP | 0 806 520 A1 | 11/1997 |
| EP | 0 836 928 A1 | 4/1998 |

| | | |
|---|---|---|
| EP | 1 099 539 | 5/2001 |
| EP | 1 157 818 A1 | 11/2001 |
| EP | 1 321 287 A2 | 6/2003 |
| GB | 2 132 141 | 7/1984 |
| GB | 2 225 745 | 11/1992 |
| WO | WO 96/18771 | 6/1996 |
| WO | WO 01/48314 | 7/2001 |
| WO | WO 01/48314 A1 | 7/2001 |
| WO | WO 01/48314 A2 | 7/2001 |
| WO | WO 01/48314 A3 | 12/2001 |

OTHER PUBLICATIONS

Co-pending U.S. Appl. No. 10/808,431, filed Mar. 25, 2004 (now U.S. Patent No. 7,182,838).
Co-pending U.S. Appl. No. 10/986,034, filed Nov. 12, 2004 (now U.S. Patent No. 7,326,322).
Co-pending U.S. Appl. No. 10/635,663, filed Aug. 6, 2003 (now U.S. Patent No. 7,037,406).
Co-pending U.S. Appl. No. 10/236,993, filed Sep. 5, 2002 (now U.S. Patent No. 6,887,349).
Co-pending U.S. Appl. No. 10/036,770, filed Dec. 21, 2001 (now U.S. Patent No. 6,733,626).
U.S. Appl. No. 10/235,197, filed Sep. 5, 2002.
U.S. Appl. No. 09/709,185, filed Nov. 9, 2002 (now U.S. Patent No. 6,455,129).
U.S. Appl. No. 10/808,432, filed Mar. 25, 2004 (now U.S. Patent No. 6,989,706).
U.S. Appl. No. 11/294,245, filed Dec. 5, 2005 (now U.S. Patent No. 7,294,231).
Co-pending U.S. Appl. No. 11/611,954, filed Dec. 18, 2006.
Co-pending U.S. Appl. No. 11/974,162, filed Oct. 11, 2007 (now U.S. Patent No. 7,531,062).
Office Action dated Nov. 2, 2005 in U.S. Appl. No. 10/808,431.
Office Action dated Sep. 18, 2006 in U.S. Appl. No. 10/808,431.
Office Action dated Apr. 24, 2006 in U.S. Appl. No. 10/808,431.
Office Action dated Aug. 1, 2005 in U.S. Appl. No. 10/986,034.
Office Action dated Sep. 29, 2005 in U.S. Appl. No. 10/986,034.
Office Action dated Jan. 9, 2006 in U.S. Appl. No. 10/986,034.
Office Action dated Jun. 12, 2006 in U.S. Appl. No. 10/986,034.
Office Action dated Jul. 25, 2006 in U.S. Appl. No. 10/986,034.
Office Action dated Mar. 31, 2004 in U.S. Appl. No. 10/236,993.
Office Action dated Aug. 26, 2004 in U.S. Appl. No. 10/236,993.
Office Action dated Jun. 19, 2003 in U.S. Appl. No. 10/036,770.
Office Action dated Jan. 5, 2004 in U.S. Appl. No. 10/036,770.
Office Action dated May 23, 2005 in U.S. Appl. No. 10/635,663.
Office Action dated Sep. 6, 2005 in U.S. Appl. No. 10/635,663.
Office Action dated Apr. 4, 2005 in U.S. Appl. No. 10/808,432.
Office Action dated Sep. 28, 2005 in U.S. Appl. No. 10/808,432.
Office Action dated Dec. 1, 2009 in U.S. Appl. No. 11/611,954.
Office Action dated May 5, 2009 in U.S. Appl. No. 11/611,954.
International Search Report dated Apr. 26, 1996 for Application No. PCT/FR 95/01681.
International Search Report dated Jul. 13, 2001 for Application No. PCT/EP 00/13005.
European Search Report dated Aug. 8, 2003, for Application No. EP 02 25 8801.
European Search Report dated Jul. 22, 1997 for Application No. EP 97 30 3190.
Smook, G.A., Handbook for Pulp and Paper Technologists, p. 339 (1992).
English-language translation of WO 01/48314, dated Jul. 5, 2001.

* cited by examiner

SECTION A-A

SIDE VIEW

MD

MD

AT .032 ENGAGEMENT 42.5 MILS
.004905907 CLEARANCE

7° WALL ANGLE CENTERED ALIGNMENT 42.5 MILS
.003910592 CLEARANCE

9° WALL ANGLE CENTERED ALIGNMENT 42.5 MILS
.003115702 CLEARANCE

11° WALL ANGLE CENTERED ALIGNMENT

AT .028 ENGAGEMENT 42.5 MILS
.006535076 CLEARANCE

7° WALL ANGLE CENTERED ALIGNMENT 42.5 MILS
.005539761 CLEARANCE

9° WALL ANGLE CENTERED ALIGNMENT 42.5 MILS
.004744871 CLEARANCE

11° WALL ANGLE CENTERED ALIGNMENT

AT .024 ENGAGEMENT

7° WALL ANGLE CENTERED ALIGNMENT

9° WALL ANGLE CENTERED ALIGNMENT

11° WALL ANGLE CENTERED ALIGNMENT

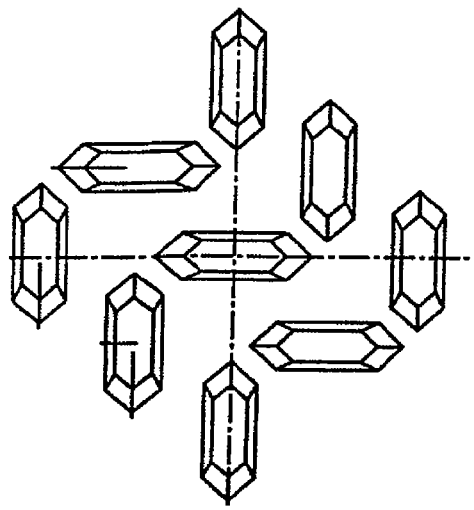
FIG. 16B
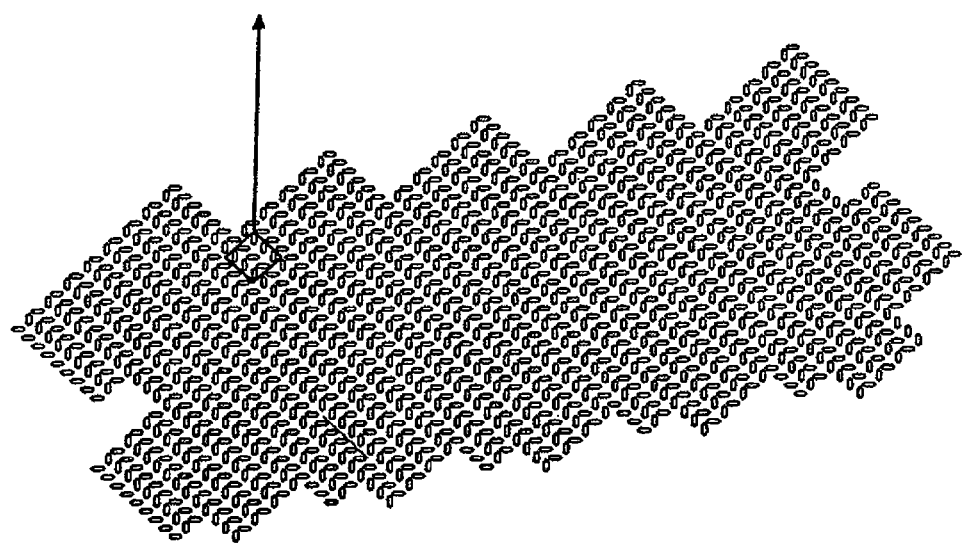
FIG. 16A
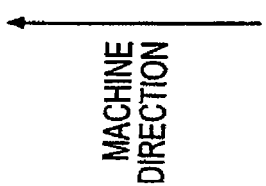
MACHINE DIRECTION

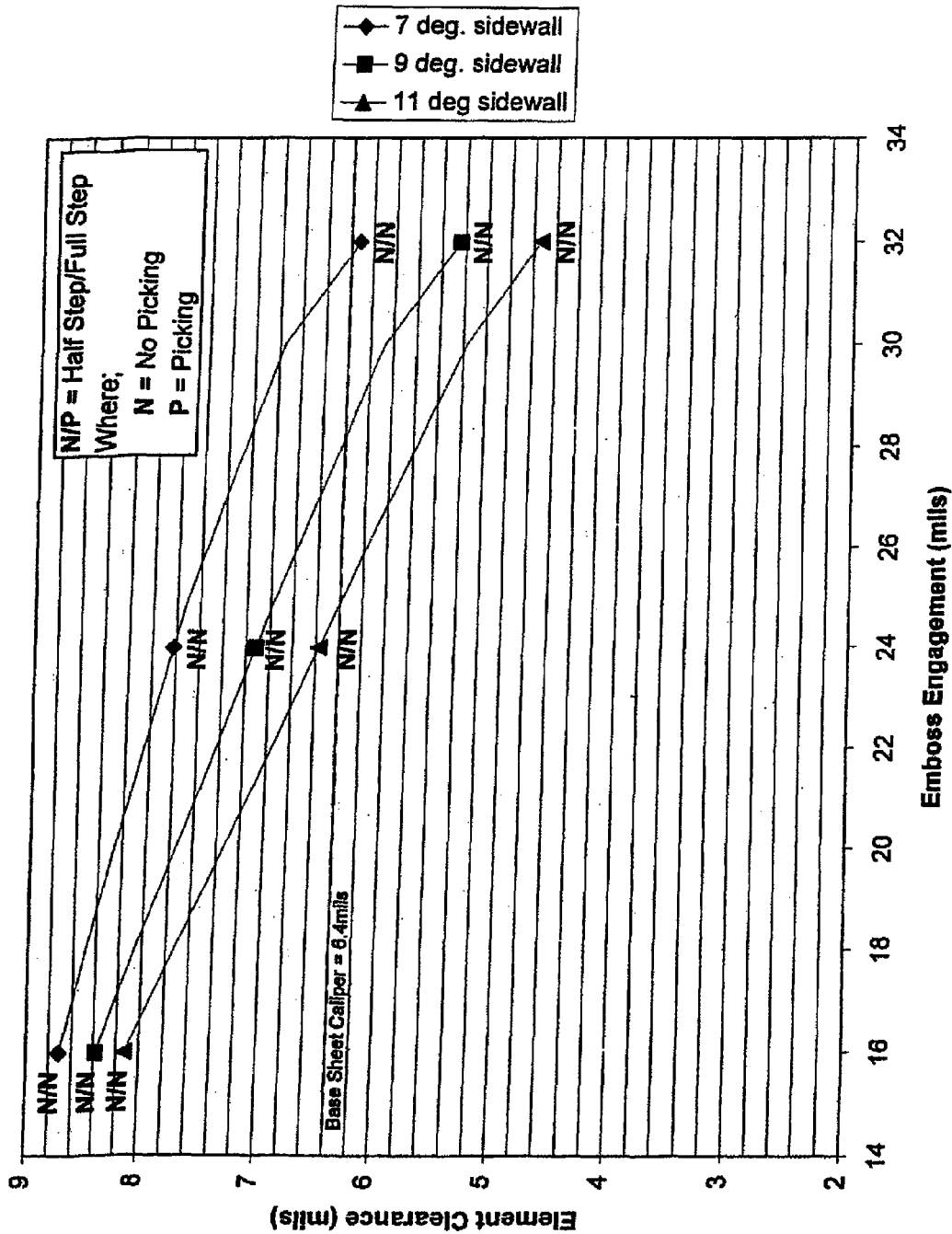

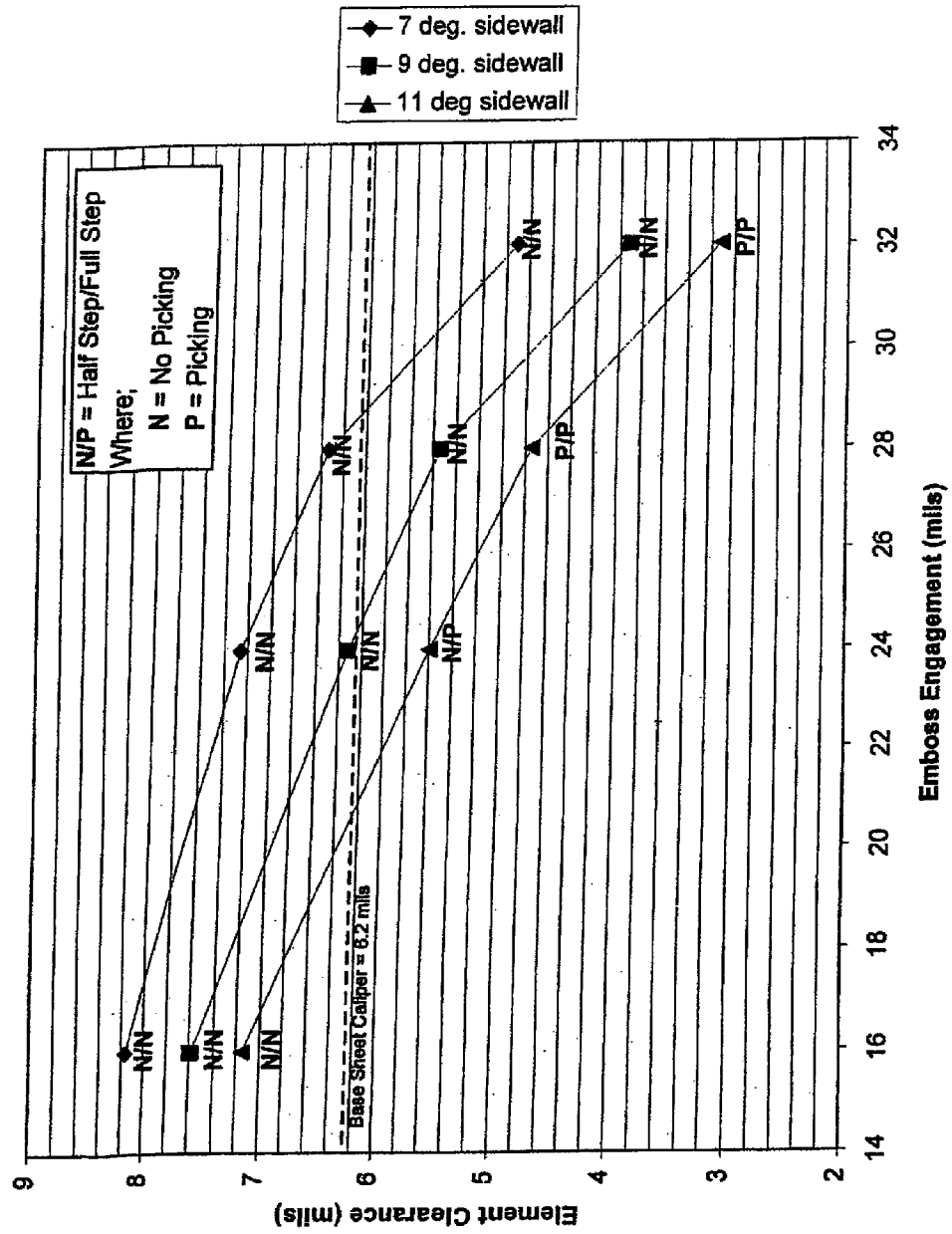

APPARATUS AND METHOD FOR DEGRADING A WEB IN THE MACHINE DIRECTION WHILE PRESERVING CROSS-MACHINE DIRECTION STRENGTH

This is a continuation of application Ser. No. 11/611,954, filed Dec. 18, 2006, now U.S. Pat. No. 7,857,941, which is a divisional of application Ser. No. 10/808,431, filed Mar. 25, 2004, now U.S. Pat. No. 7,182,838, which is a divisional of application Ser. No. 10/036,770, filed Dec. 21, 2001, now U.S. Pat. No. 6,733,626.

FIELD OF THE INVENTION

The present invention relates to an apparatus and method for embossing a moving web of material, such as paper, to create a functional controlled degradation of the machine direction strength of the web while limiting degradation of the cross-machine direction strength of the web. In particular, the present invention relates to an apparatus and method for embossing a moving web using an embossing system having perforate embossing elements oriented to define perforating nips substantially oriented in the cross-machine direction to improve the flexibility, feel, bulk, and absorbency of the paper.

BACKGROUND OF THE INVENTION

Embossing is the act of mechanically working a substrate to cause the substrate to conform under pressure to the depths and contours of a patterned embossing roll. Generally the web is passed between a pair of embossing rolls that, under pressure, form contours within the surface of the web. During an embossing process, the roll pattern is imparted onto the web at a certain pressure and/or penetration. In perforate embossing the embossing elements are configured such that at least a portion of the web located between the embossing elements is perforated. As used herein, generally, "perforated" refers to the existence of either (1) a macro-scale through aperture in the web or (2) when a macro-scale through aperture does not exist, at least incipient tearing such as would increase the transmittivity of light through a small region of the web or would decrease the machine direction strength of a web by at least 15% for a given range of embossing depths.

Embossing is commonly used to modify the properties of a web to make a final product produced from that web more appealing to the consumer. For example, embossing a web can improve the softness, absorbency, and bulk of the final product. Embossing can also be used to impart an appealing pattern to a final product.

Embossing is carried out by passing a web between two or more embossing rolls, at least one of which carries the desired emboss pattern. Known embossing configurations include rigid-to-resilient embossing and rigid-to-rigid embossing.

In a rigid-to-resilient embossing system, a single or multi-ply substrate is passed through a nip formed between a roll whose substantially rigid surface contains the embossing pattern as a multiplicity of protuberances and/or depressions arranged in an aesthetically-pleasing manner, and a second roll, whose substantially resilient surface can be either smooth or also contain a multiplicity of protuberances and/or depressions which cooperate with the rigid surfaced patterned roll. Commonly, rigid rolls are formed with a steel body which is either directly engraved upon or which can contain a hard rubber-covered, or other suitable polymer, surface (directly coated or sleeved) upon which the embossing pattern is formed by any convenient method such as, for example, being laser engraved. The resilient roll may consist of a steel core provided with a resilient surface, such as being directly covered or sleeved with a resilient material such as rubber, or other suitable polymer. The rubber coating may be either smooth or engraved with a pattern. The pattern on the resilient roll may be either a mated or a non-mated pattern with respect to the pattern carried on the rigid roll.

In the rigid-to-rigid embossing process, a single-ply or multi-ply substrate is passed through a nip formed between two substantially rigid rolls. The surfaces of both rolls contain the pattern to be embossed as a multiplicity of protuberances and/or depressions arranged into an aesthetically-pleasing manner where the protuberances and/or depressions in the second roll cooperate with those patterned in the first rigid roll. The first rigid roll may be formed, for example, with a steel body which is either directly engraved upon or which can contain a hard rubber-covered, or other suitable polymer, surface (directly coated or sleeved) upon which the embossing pattern is engraved by any conventional method, such as by laser engraving. The second rigid roll can be formed with a steel body or can contain a hard rubber covered, or other suitable polymer, surface (directly coated or sleeved) upon which any convenient pattern, such as a matching or mated pattern, is conventionally engraved or laser-engraved. In perforate embossing, a rigid-to-rigid embossing system is typically used. However, a rigid-resilient configuration can also be used for perforate embossing.

When substantially rectangular embossing elements have been employed in perforate embossing, the embossing elements on the embossing rolls have generally been oriented so that the long direction axis, i.e., the major axis, of the elements is in the machine direction. That is, the major axis of the elements is oriented to correspond to the direction of the running web being embossed. These elements are referred to as machine direction elements. As a result, the elements produce perforations which extend primarily in the machine direction and undesirably decrease the strength of the web in the cross-machine direction. This orientation improves absorbency and softness, but can degrade, i.e., reduce the strength of, the web primarily in the cross-machine direction while less significantly degrading the strength of the web in the machine direction. As a result, the tensile strength of the web in the cross-machine direction is reduced relatively more, on a percentage basis, than that of the machine direction. In addition, the cross-machine direction strength of the base sheet is typically less than that of the machine direction strength. As a result, by embossing with machine direction elements, the cross-machine direction strength is even further weakened and, accordingly, because the finished product will fail in the weakest direction, the product will be more likely to fail when stressed in the cross-machine direction. Often, it is preferred that the web is "square," i.e., has a machine direction/cross-machine direction tensile ratio close to 1.0.

Cross-machine direction tensile strength can be associated with consumer preference for paper toweling. In particular, consumers prefer a strong towel, of which cross-machine direction and machine direction strength are two components. Because the un-embossed base sheet is typically much stronger in the machine direction than the cross-machine direction, a process is desired which results in both improved absorbency and softness without sustaining excessive losses in cross-machine direction tensile strength.

The present invention addresses at least the above described problem by providing at least two embossing rolls, wherein at least a portion of the elements are oriented to provide perforating nips which are substantially in the cross-machine direction and are configured to perforate the web, thereby allowing relatively greater degradation, i.e., a reduction of strength, of the web in the machine direction while preserving more of the cross-machine direction strength.

Further advantages of the invention will be set forth in part in the description which follows and in part will be apparent from the description or may be learned by practice of the invention. The advantages of the invention may be realized and attained by means of the instrumentalities and combinations particularly pointed out in the appended claims.

SUMMARY OF THE INVENTION

As embodied and broadly described herein, the invention includes an embossing system for embossing and perforating at least a portion of a web comprising a first embossing roll having embossing elements and at least a second embossing roll having embossing elements, wherein juxtaposition and engagement of the first and second embossing rolls define a plurality of perforate nips for embossing and perforating the web and wherein at least a predominate number of the embossing elements are configured so as to produce perforating nips which are substantially oriented in the cross-machine direction. In one embodiment, the invention further includes an embossing system wherein substantially all of the embossing elements of the first and second embossing rolls produce perforating nips which are substantially oriented in the cross-machine direction. Further, in a preferred embodiment, the cross-machine embossing elements are at an angle of 85 to 95° from the machine direction.

In another embodiment, the invention includes an embossing system for embossing at least a portion of a web comprising a first embossing roll and at least a second embossing roll, wherein each of the first and second embossing rolls has at least one juxtaposable embossing element capable of producing a perforating nip substantially oriented in the cross-machine direction, thereby defining a cross-machine direction perforate nip between the cross-machine direction elements for embossing and perforating the web, and wherein at least a substantial portion of the cross-machine direction elements have at least the ends beveled.

In yet another embodiment, the invention includes an embossing system for embossing and perforating at least a portion of a web comprising a first embossing roll and at least a second embossing roll, wherein each of the first and second embossing rolls has at least one juxtaposable element capable of producing a perforating nip substantially oriented in the cross-machine direction, thereby defining a cross-machine direction perforate nip between the cross-machine direction elements for embossing and perforating the web, and wherein the cross-machine direction elements have sidewall angles, the angle between the sidewall and the radial direction on the cross-machine direction sides of the element, juxtaposed so as to be capable of producing a shear line, of less than about 20°. In one embodiment the cross-machine direction elements have cross-machine direction sidewall angles of less than about 17°. In another embodiment the cross-machine direction elements have cross-machine direction sidewall angles of less than about 14°. In a preferred embodiment, the cross-machine direction elements have cross-machine direction sidewall angles of less than about 11°. In a further preferred embodiment the cross-machine direction elements have cross-machine direction sidewall angles of from about 7° to 11°.

In yet another embodiment, the invention includes a method for embossing and perforating at least a portion of a web comprising providing a first embossing roll having embossing elements and providing at least a second embossing roll having embossing elements, wherein at least a predominate number of the embossing elements, when juxtaposed such that they are capable of producing perforate nips, are substantially oriented in the cross-machine direction and wherein the first and second embossing rolls define a perforate nip for embossing and perforating the web and passing the web between the first and second embossing rolls wherein the first and second embossing rolls are configured to result in an element clearance that will achieve a non-picking clearance while achieving at least a 15% reduction in the machine direction tensile strength of the web. We have found that it is desirable to exert special care to control the circumferential alignment of the two rolls to alleviate picking which may result from drift caused by local variances in roll diameter or gearing from the ideal.

In still yet another embodiment, the invention includes a method for reducing the tensile ratio of a web by embossing and perforating the web comprising passing a web through an embossing system, wherein the embossing system comprises a first embossing roll having embossing elements and at least a second embossing roll having embossing elements, wherein the first and second embossing rolls define a plurality of perforating nips for embossing and perforating the web and wherein at least a predominant number of the perforating nips which are substantially oriented in the cross-machine direction. In one embodiment, the invention further includes an embossing system wherein substantially all of the embossing elements of the first and second embossing rolls produce perforating nips which are substantially oriented in the cross-machine direction. Further, in a preferred embodiment, the cross-machine embossing elements are at an angle of 85-95° from the machine direction.

In yet another embodiment, the invention includes a method for reducing the tensile ratio of a web by embossing and perforating the web comprising passing a web through an embossing system, wherein the embossing system comprises a first embossing roll and at least a second embossing roll, wherein each of the first and second embossing rolls has at least one juxtaposable embossing element capable of producing a perforating nip substantially oriented in the cross-machine direction, thereby defining a cross-machine direction perforate nip between the cross-machine direction elements for embossing and perforating the web and wherein at least a substantial portion of the cross-machine direction elements have at least the ends beveled.

In still yet another embodiment, the invention includes a method for reducing the tensile ratio of a web by embossing and perforating the web comprising, passing a web through an embossing system, wherein the embossing system comprises a first embossing roll and at least a second embossing roll, wherein each of the first and second embossing rolls has at least one juxtaposable embossing element capable of producing a perforating nip substantially oriented in the cross-machine direction, thereby defining a cross-machine direction perforate nip between the cross-machine direction elements for embossing and perforating the web and wherein the cross-machine direction elements have cross-machine direction sidewall angles of less than about 20°. In one embodiment the cross-machine direction elements have cross-machine direction sidewall angles of less than about 17°. In another embodiment the cross-machine direction elements have cross-machine direction sidewall angles of less than about 14°. It is preferred that the cross-machine direction elements have cross-machine direction sidewall angles of less than about 11°. It is further preferred that the cross-machine direction elements have cross-machine direction sidewall angles of from about 7° to 11°.

In another embodiment, the invention includes a method for reducing the tensile ratio of a web by embossing and perforating the web comprising passing a web through an embossing system, wherein the embossing system comprises a first embossing roll having embossing elements and at least a second embossing roll having embossing elements, wherein the first and second embossing rolls define a perforate nip for embossing and perforating the web and wherein the first and second embossing rolls are configured to result in an element clearance that will achieve a non-picking clearance.

The invention further includes a perforate embossed web having a plurality of cross-machine direction oriented perforations wherein the embossed web has a tensile ratio of less than about 1.2. The invention further includes a perforate embossed web having a transluminance ratio (as defined hereinafter) of at least 1.005. Still further, the invention includes a wet-laid cellulosic perforate embossed web having perforate embossments extending predominately in the cross-machine direction.

Finally, the invention includes a method of embossing and perforating the web comprising passing a web through an embossing system, wherein the embossing system comprises a first embossing roll having embossing elements and at least a second embossing roll having embossing elements, wherein the first and second embossing rolls define a plurality of perforate nips for embossing and perforating the web, and wherein the tensile ratio of the web is reduced.

The accompanying drawings, which are incorporated herein and constitute a part of this specification, illustrate an embodiment of the invention, and, together with the description, serve to explain the principles of the invention.

BRIEF DESCRIPTION OF THE DRAWINGS

FIGS. 16A-B illustrate embossing rolls having both cross-machine direction and machine direction elements according to an embodiment of the present invention.

FIG. 19 is a graph illustrating the effect on fiber picking according to certain embodiments of the present invention.

FIG. 20 is a graph illustrating the effect on fiber picking according to certain embodiments of the present invention.

DETAILED DESCRIPTION

Reference will now be made in detail to the preferred embodiments of the present invention, examples of which are illustrated in the accompanying drawings.

The present invention can be used to emboss a variety of types of wet-laid cellulosic webs including paper, and the like. The webs can be continuous or of a fixed length. Moreover, embossed webs can be used to produce any art recognized product, including, but not limited to, paper towels, napkins, tissue, or the like. Moreover, the resulting product can be a single ply or a multi-ply paper product, or a laminated paper product having multiple plies. In addition, the present invention can be used with a web made from virgin furnish, recycled furnish, or a web containing both virgin and recycled furnish, synthetic fibers, or any combination thereof.

In accordance with the invention, as broadly described, the converting process includes an embossing system of at least two embossing rolls, the embossing rolls defining at least one nip through which a web to be embossed is passed. The embossing elements are patterned to create perforations in the web as it is passed through the nip.

Figure 18:
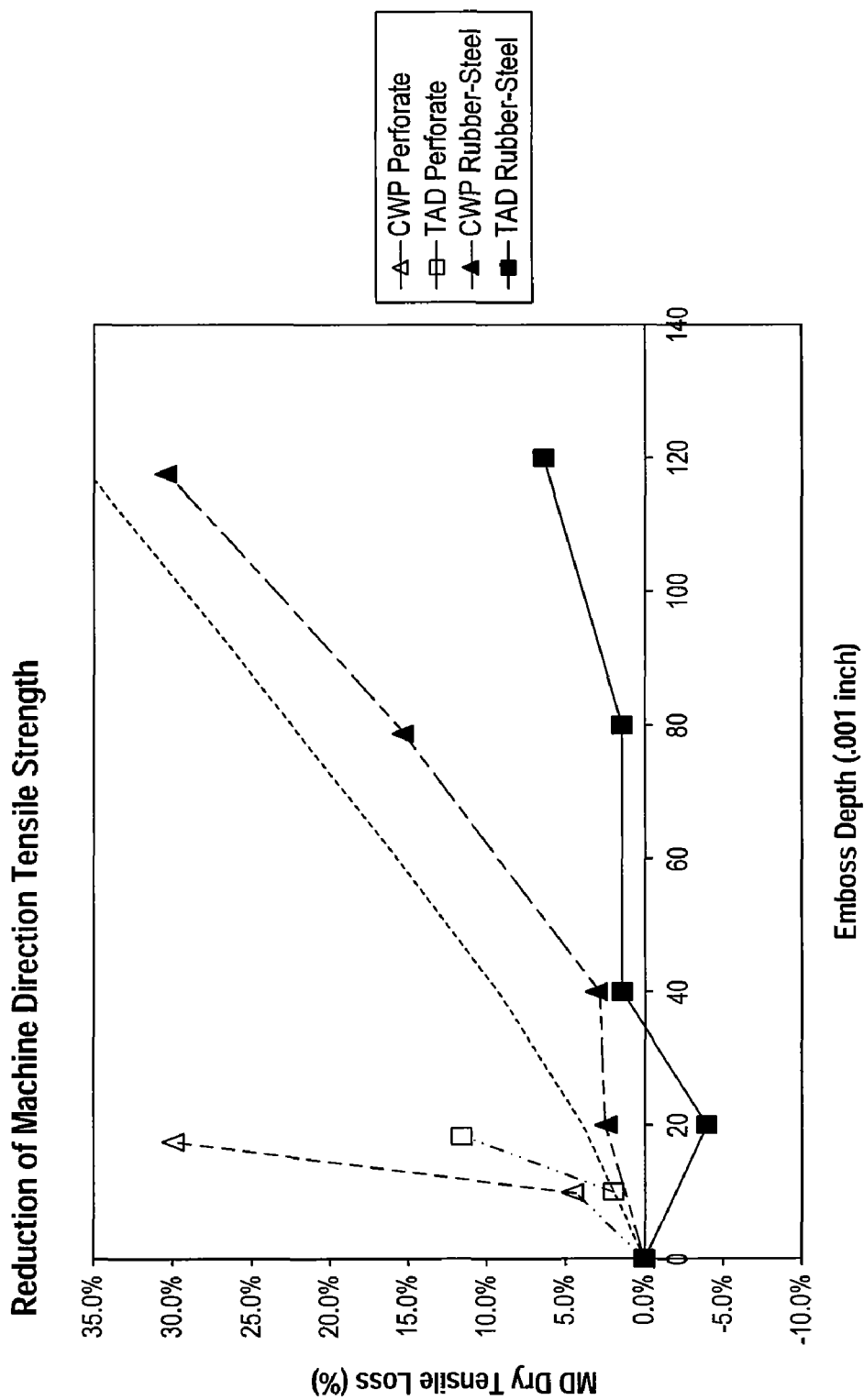
FIG. 18 is a graph illustrating the reduction in machine direction tensile strength according to an embodiment of the present invention.

Generally, for purposes of this invention, perforations are created when the strength of the web is locally degraded between two bypassing embossing elements resulting in either (1) a macro scale through-aperture or (2) in those cases where a macro scale through-aperture is not present, at least incipient tearing, where such tearing would increase the transmittivity of light through a small region of the web or would decrease the machine direction strength of a web by at least 15% for a given range of embossing depths. FIG. 18 depicts a comparison of the effects on reduction of strength in the machine direction when perforate embossing a web, as defined herein, and non-perforate embossing a web. In particular, a conventional wet pressed base sheet was perforate embossed between two steel rolls. The same base sheet was non-perforate embossed in a rubber to steel configuration. In addition, a through-air-dried base sheet was also perforate and non-perforate embossed. The reduction in machine direction strength was measured for each of the sheets. The results are plotted on FIG. 18.

As shown in FIG. 18, when non-perforate embossing either a CWP or TAD web to depths of up to 40 mils, the reduction of paper strength in the machine direction is less than 5%. And, when non-perforate embossing either of the CWP or TAD webs at a depth of 80 mils, the reduction of strength of the web is less than 15%. When perforate embossing a web as disclosed in this invention, a greater reduction in strength of the web can be achieved. In the example set forth herein, strength reductions of greater than 15% are achieved when perforate embossing at depths of at least about 15 mils as compared to rubber to steel embossing which can result in these strength losses at emboss depths of over 60 mils. Accordingly, for purposes of this invention, perforation is specifically defined as locally degrading the strength of the web between two bypassing embossing elements resulting in either (1) the formation of a macro scale through-aperture or (2) when a macro scale through-aperture is not formed, at least incipient tearing, where such tearing would either increase the transmittivity of light through a small region of the web or would decrease the machine direction strength of a web by at least the percentages set forth in FIG. 18, wherein the "at least" percentages are indicated by the dashed line.

Not being bound by theory, we believe that the superior strength reduction results achieved using the present invention are due to the location of the local degradation of the web when perforate embossing as compared to when non-perforate embossing. When a web is embossed, either by perforate or non-perforate methods, the portion of the web subject to the perforate or non-perforate nip is degraded. In particular, as a web passes through a non-perforate nip for embossing, the web is stressed between the two embossing surfaces such that the fiber bonds are stretched and sometimes, when the web is over embossed, which is not desired when non-perforate embossing a web, the bonds are torn or broken. When a web is passed through a perforate nip, the web fiber bonds are at least incipiently torn by the stresses caused by the two bypassing perforate elements. As stated above, however, one difference between the two methods appears to be in the location of the at least incipient tearing.

Figure 17A:
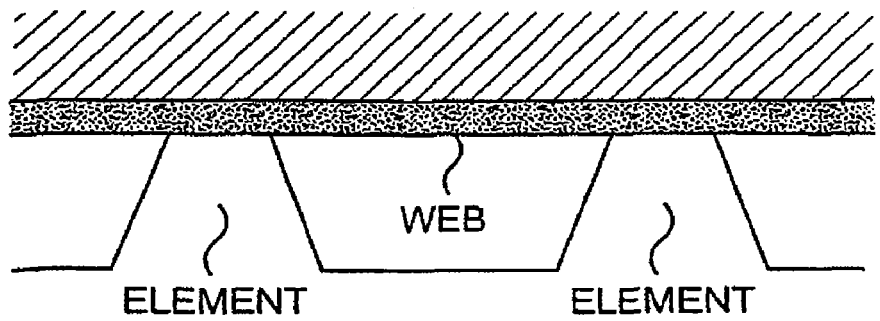
FIGS. 17A-C illustrate the effects of over embossing a web portion in the machine direction and cross-machine direction when using rigid to resilient embossing as compared to perforate embossing a web as in FIG. 17D.
Figure 17B:
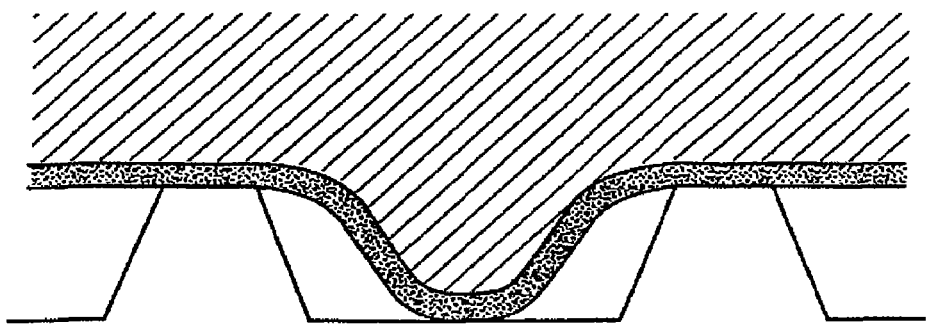
Figure 17C:
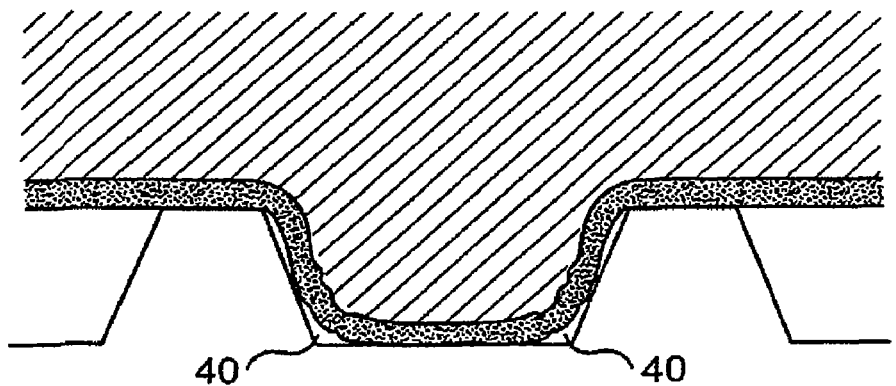

When a web is over-embossed in a rubber to steel configuration, the male steel embossing elements apply pressure to the web and the rubber roll, causing the rubber to deflect away from the pressure, while the rubber also pushes back. As the male embossing elements roll across the rubber roll during the embossing process, the male elements press the web into the rubber roll which causes tension in the web at the area of the web located at the top edges of the deflected rubber roll, i.e., at the areas at the base of the male embossing elements. When the web is over-embossed, tearing can occur at these high-tension areas. More particularly, FIGS. 17A-C depict rubber to steel embossing of a web at various embossing depths. FIG. 17A depicts embossing of a web at approximately 0 mils. In this configuration the rubber roll pins the web at the points where the web contacts the steel roll element tops. Typically no tearing will occur in this configuration. In FIG. 17B, where the embossing depth is approximately the height of the steel embossing element, the web is pinned at the element tops and at a point between the bases of the adjacent steel elements. As with the configuration depicted in FIG. 17A, tearing does not typically occur in this configuration for conventional embossing procedures. FIG. 17C depicts an embossing depth comparable to or greater than the height of the steel element. In this configuration, the "free span" of the web, i.e., the sections of the web that are not pinned between the rubber and steel rolls, becomes shorter as the rubber material fills the area between the adjacent elements. When web rupturing occurs, it tends to occur near the last location where web movement is possible; that is, the area of degradation 40 is the last area that is filled by the rubber material, namely the corners where the bases of the elements meet the surface of the emboss roll.

Figure 17D:
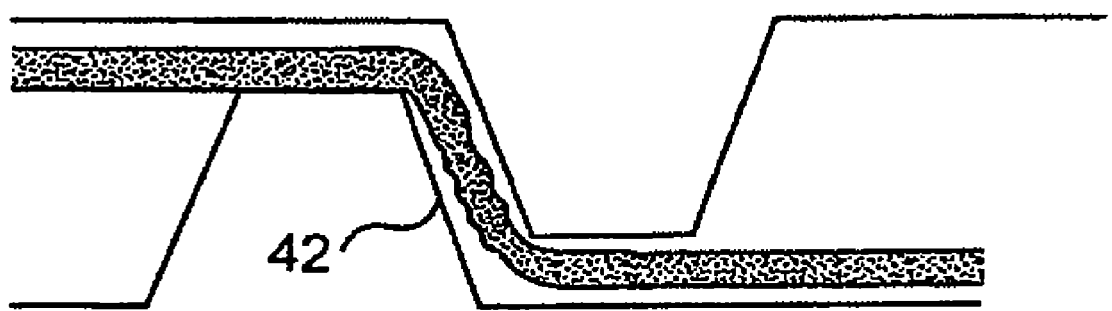

When a web is perforate embossed, on the other hand, the areas of degradation 42, as shown in FIG. 17D, are located along the sides of the perforate embossing element. It appears that as a result of this difference the degradation of the web and the resultant reduction of web strength is dramatically different.

In one embodiment according to the present invention, the embossing rolls have substantially identical embossing element patterns, with at least a portion of the embossing elements configured such that they are capable of producing perforating nips which are capable of perforating the web. As the web is passed through the nip, an embossing pattern is imparted on the web. It is preferred that the embossing rolls be either steel or hard rubber, or other suitable polymer. The direction of the web as it passes through the nip is referred to as the machine direction. The transverse direction of the web that spans the emboss roll is referred to as the cross-machine direction. It is further preferred that a predominant number, i.e., at least 50% or more, of the perforations are configured to be oriented such that the major axis of the perforation is substantially oriented in the cross-machine direction. An embossing element is substantially oriented in the cross-machine direction when the long axis of the perforation nip formed by the embossing element is at an angle of from about 60° to 120° from the machine direction of the web.

In an embodiment according to the present invention, and as shown in FIG. 1, the converting process includes an embossing system 20 of two embossing rolls 22 defining a nip 28 through which the web 32 to be embossed is passed. According to one embodiment, the embossing rolls 22 are matched embossing rolls. The embossing rolls can be, for example, either steel or hard rubber, or other suitable polymer. The embossing rolls 22 have at least a portion of embossing elements 34 oriented such that the major axis of the elements 34 is in the cross-machine direction, i.e., the elements are in the cross-machine direction. It is possible to envisage configurations in which perforations extending in the cross-machine direction are formed by elements which are longer in the machine direction, although such a configuration would normally be sub-optimal as it would compromise the overall number of perforations which could be formed in the web. Accordingly, when we discuss elements oriented in the cross-machine direction, we are referring to elements that are configured such that the orientation of the perforation formed by those elements extends in the cross-machine direction, irrespective of the shape of the remainder of the element not contributing to the shape of the nip, whether the element be male or female. While the embossing rolls 22 can also have embossing elements oriented such that the major axis of the elements is in the machine direction, a predominant number, i.e., at least 50% or more, of the elements 34 should be oriented such that they are capable of producing perforating nips extending in the cross-machine direction. In another embodiment, substantially all, i.e., at least more than 75%, of the elements 34 are oriented such that they are capable of producing perforating nips extending in the cross-machine direction. In yet another embodiment, all of the elements are oriented in the cross-machine direction. Moreover, at least about 25% of the cross-machine direction elements are perforating elements. In a preferred embodiment, all of the cross-machine direction elements are perforating elements. Thus, when the web passes through the embossing rolls 22, at least a portion of the cross-machine direction elements are aligned such that the web is perforated such that at least a portion of the perforations are substantially oriented in the cross-machine direction.

The end product characteristics of a cross-machine direction perforated embossed product can depend upon a variety of factors of the embossing elements that are imparting a pattern on the web. These factors can include one or more of the following: embossing element height, angle, shape, including sidewall angle, spacing, engagement, and alignment, as well as the physical properties of the rolls, base sheet, and other factors. Following is a discussion of a number of these factors.

An individual embossing element 34 has certain physical properties, such as height, angle, and shape, that affect the embossing pattern during an embossing process. The embossing element can be either a male embossing element or a female embossing element. The height of an element 34 is the distance the element 34 protrudes from the surface of the embossing roll 22. It is preferred that the embossing elements 34 have a height of at least about 15 mils. In one embodiment according to the present invention, the cross-machine direction elements 34 have a height of at least about 30 mils. In another embodiment of the present invention, the cross-machine direction elements 34 have a height of greater than about 45 mils. In yet another embodiment of the invention, the cross-machine elements have a height of greater than about 60 mils. In yet another embodiment, a plurality of the elements 34 on the roll have at least two regions having a first region having elements having a first height and at least a second region having elements having a second height. In a preferred embodiment, the elements 34 have a height of between about 30 to 65 mils. Those of ordinary skill in the art will understand that there are a variety of element heights that can be used, depending upon a variety of factors, such as the type of web being embossed and the desired end product.

The angle of the cross-machine direction elements 34 substantially defines the direction of the degradation of the web due to cross-machine perforate embossing. When the elements 34 are oriented at an angle of about 90° from the machine direction, i.e., in the absolute cross-machine direction, the perforation of the web can be substantially in the direction of about 90° from the machine direction and, thus, the degradation of web strength is substantially in the machine direction. On the other hand, when the elements 34 are oriented at an angle from the absolute cross-machine direction, degradation of strength in the machine direction will be less and degradation of strength in the cross-machine direction will be more as compared to a system where the elements 34 are in the absolute cross-machine direction.

The angle of the elements 34 can be selected based on the desired properties of the end product. Thus, the selected angle can be any angle that results in the desired end product. In an embodiment according to the present invention, the cross-machine direction elements 34 can be oriented at an angle of at least about 60° from the machine direction of the web and less than about 120° from the machine direction of the web. In another embodiment, the cross-machine direction elements 34 are oriented at an angle from at least about 75° from the machine direction of the web and less than about 105° from the machine direction of the web. In yet another embodiment, the cross-machine direction elements 34 are oriented at an angle from at least about 80° from the machine direction of the web and less than about 100° from the machine direction of the web. In a preferred embodiment, the cross-machine direction elements 34 are oriented at an angle of about 85-95° from the machine direction.

Figure 1A:
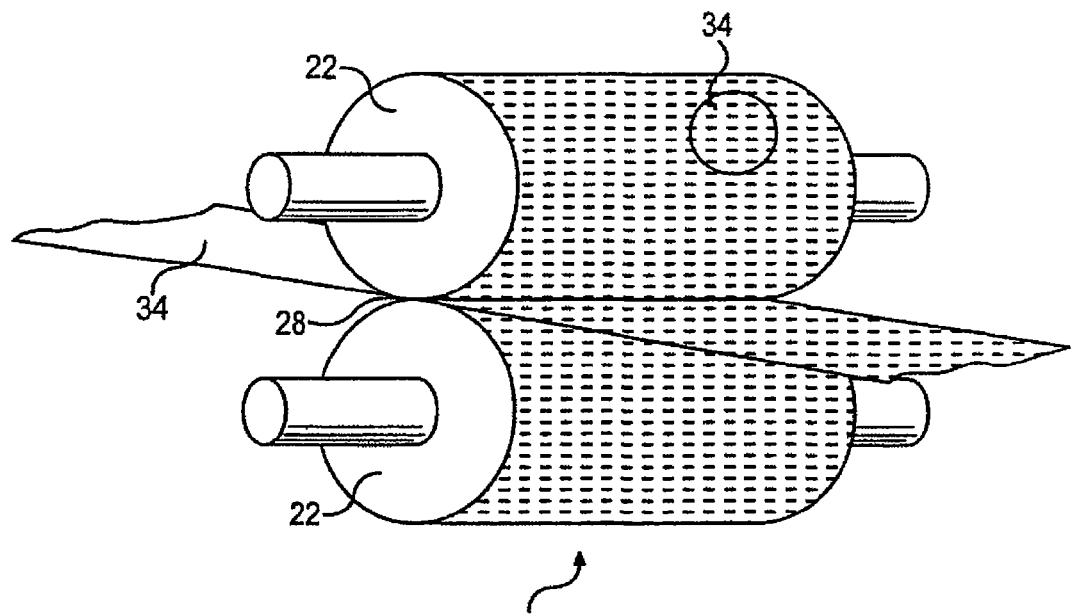
FIGS. 1A-D illustrates embossing rolls having cross-machine direction elements according to an embodiment of the present invention.
Figure 1B:
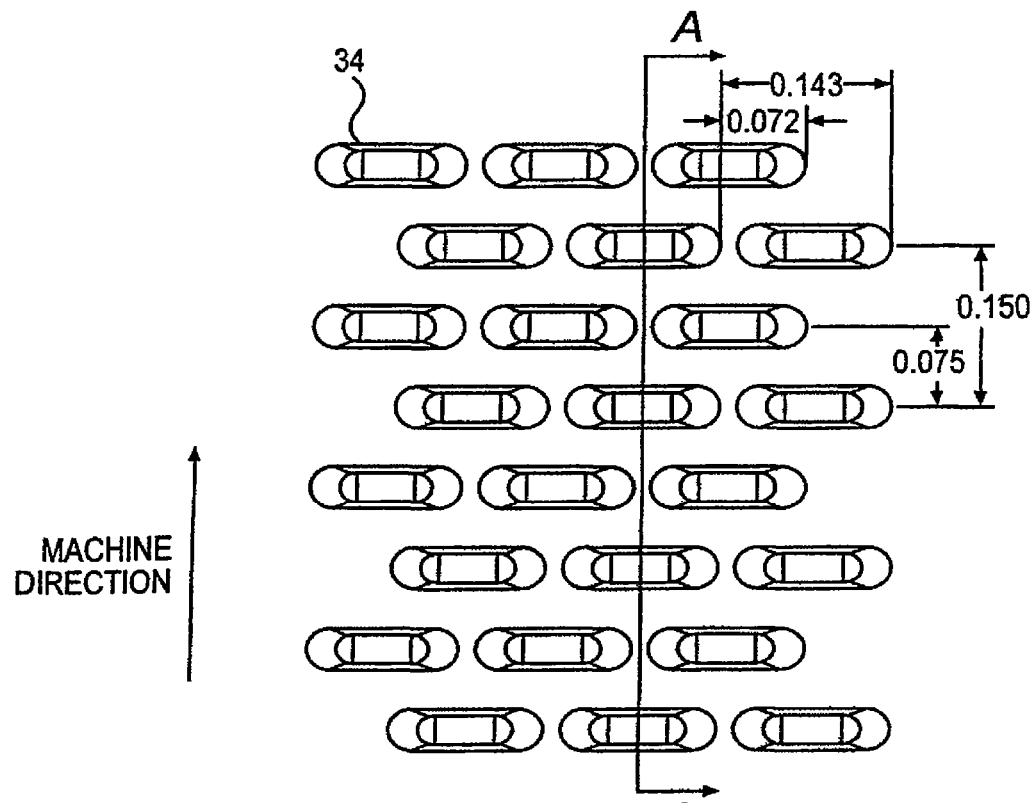
Figure 1C:
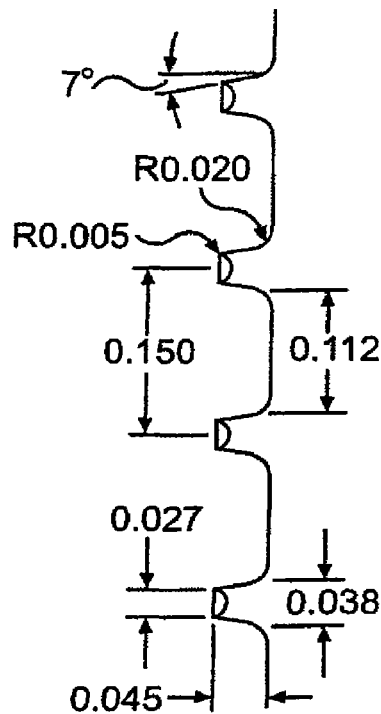
Figure 1D:
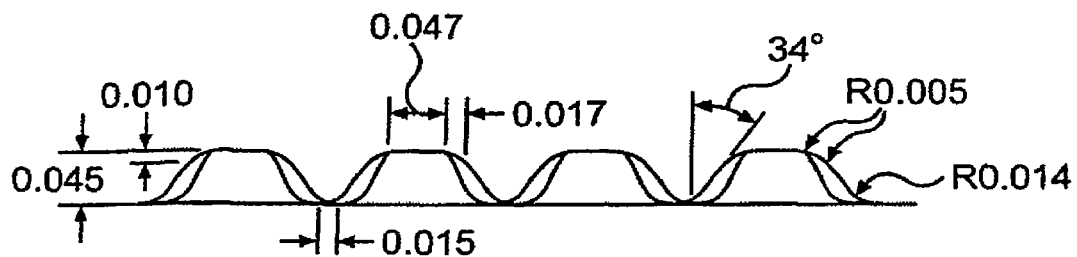
Figure 2:
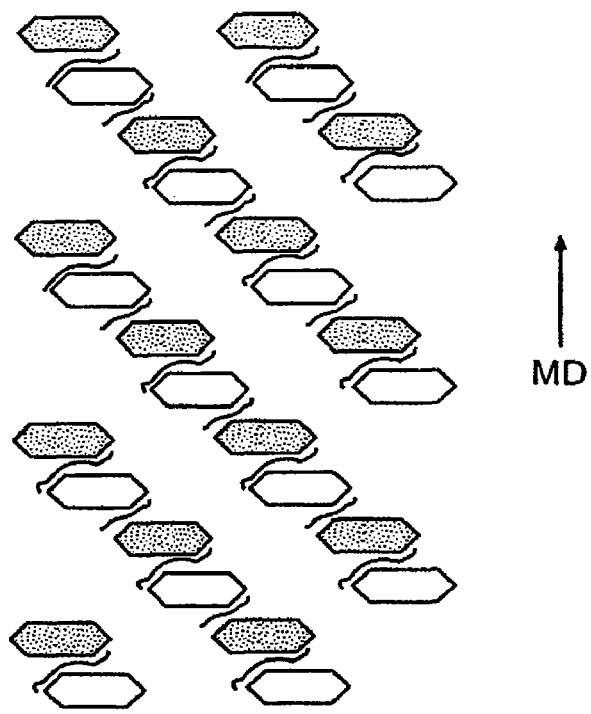
FIG. 2 illustrates cross-machine direction elements according to another embodiment of the present invention.
Figure 3:
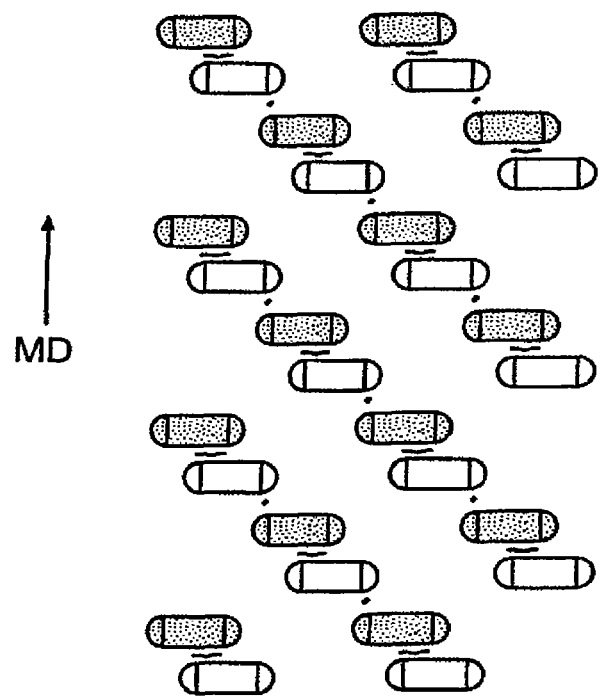
FIG. 3 illustrates cross-machine direction elements according to another embodiment of the present invention.

A variety of element shapes can be successfully used in the present invention. The element shape is the "footprint" of the top surface of the element, as well as the side profile of the element. It is preferred that the elements 34 have a length (in the cross-machine direction)/width (in the machine direction) (L/W) aspect ratio of at least greater than 1.0, however while noted above as sub-optimal, the elements 34 can have an aspect ratio of less than 1.0. It is further preferred that the aspect ratio be about 2.0. One element shape that can be used in this invention is a hexagonal element, as depicted in FIG. 2. Another element shape, termed an oval, is depicted in FIG. 3. For oval elements, it is preferred that the ends have radii of at least about 0.003" and less than about 0.030" for at least the side of the element forming a perforate nip. In one embodiment, the end radii are about 0.0135". Those of ordinary skill in the art will understand that a variety of different embossing element shapes, such as rectangular, can be employed to vary the embossing pattern.

In one embodiment, at least a portion of the elements 34 are beveled. In particular, in one embodiment the ends of a portion of the elements 34 are beveled. Oval elements with beveled edges are depicted in FIG. 1. By beveling the edges, the disruptions caused by the embossing elements can be better directed in the cross-machine direction, thereby reducing cross-machine direction degradation caused by the unintentional machine direction disruptions. The bevel dimensions can be from at least about 0.010" to at least about 0.025" long in the cross-machine direction and from at least about 0.005" to at least about 0.015" in the z-direction. Other elements, such as hexagonal elements, can be beveled, as well.

The cross-machine direction sidewall of the elements 34 defines the cutting edge of the elements 34. According to one embodiment of the present invention, the cross-machine direction sidewalls of the elements 34 are angled. As such, when the cross-machine direction sidewalls are angled, the base of the element 34 has a width that is larger than that of the top of the element. It is preferred that the cross-machine direction sidewall angle be less than about 20°. It is still further preferred that the cross-machine direction sidewall angle be less than about 17°. It is still further preferred that the cross-machine direction sidewall angle be less than about 14°. Finally, in a preferred embodiment the cross-machine direction sidewall angle is less than about 11°. It is further preferred that the cross-machine direction sidewall angle be between about 7° and 11°.

When the opposing elements 34 of the embossing rolls are engaged with each other during an embossing process, the effect on the web is impacted by at least element spacing, engagement, and alignment. When perforate embossing, the elements 34 are spaced such that the clearance between the sidewalls of elements of a pair, i.e., one element 34 from each of the opposing embossing rolls 22, creates a nip that perforates the web as it is passed though the embossing rolls 22. If the clearance between elements 34 on opposing rolls is too great, the desired perforation of the web may not occur. On the other hand, if the clearance between elements 34 is too little, the physical properties of the finished product may be degraded excessively or the embossing elements themselves could be damaged. The required level of engagement of the embossing rolls is at least a function of the embossing pattern (element array, sidewall angle, and element height), and the base sheet properties, e.g., basis weight, caliper, strength, and stretch. At a minimum, it is preferred that the clearances between the sidewalls of the opposing elements of the element pair be sufficient to avoid interference between the elements. In one embodiment, the minimum clearance is about a large fraction of the thickness of the base sheet. For example, if a conventional wet press (CWP) base sheet having a thickness of 4 mils is being embossed, the clearance can be at least about 2-3 mils. If the base sheet is formed by a process which results in a web with rather more bulk, such as, for example, a through air dried (TAD) method or by use of an undulatory creping blade, the clearance could desirably be relatively less. Those of ordinary skill in the art will be able to determine the desired element spacing of the present invention based on the factors discussed above using the principles and examples discussed further herein.

As noted above, in one embodiment it is preferred that the height of the elements 34 be at least about 30 mils, and it is further preferred that the height be from about 30 to 65 mils. Engagement, as used herein, is the overlap in the z-direction of the elements from opposing embossing rolls when they are engaged to form a perforating nip. The engagement overlap should be at least 1 mil.

Figure 12A:
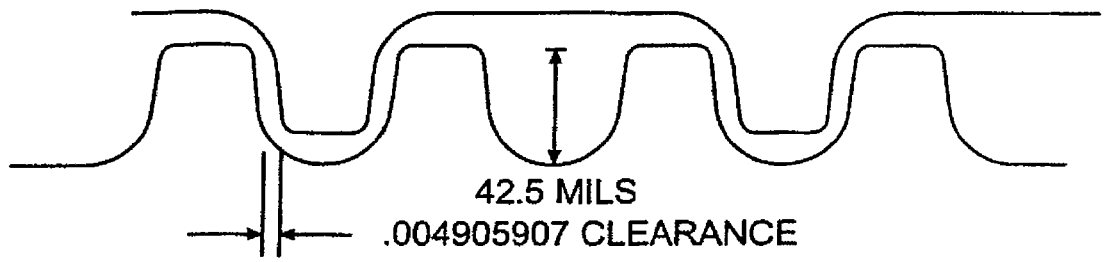
FIGS. 12A-C are side views of the cross-machine direction elements of embodiments of the present invention having differing wall angles and illustrating the effect of the differing wall angles.
Figure 12B:
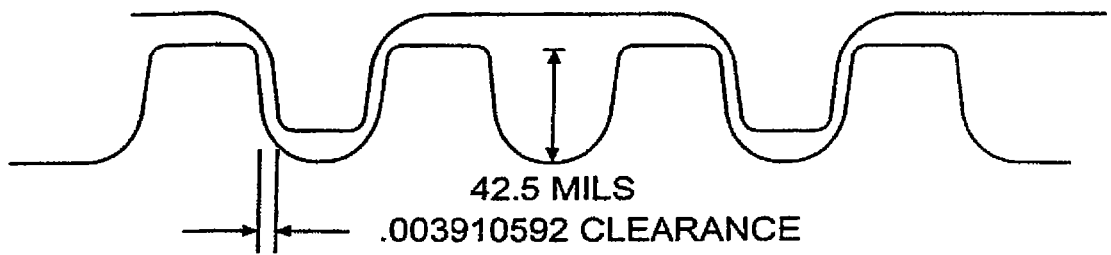
Figure 12C:
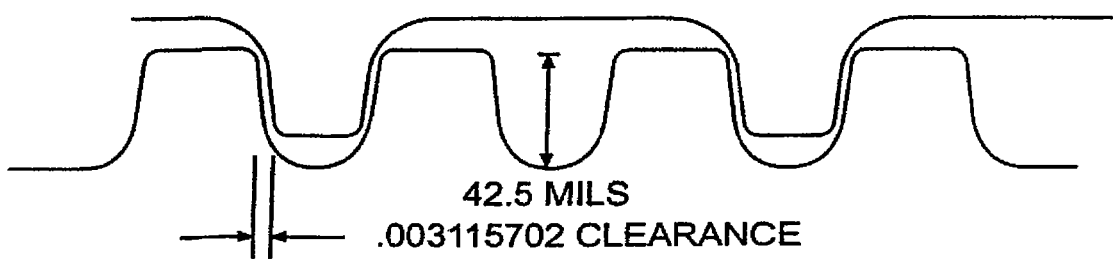
Figure 13A:
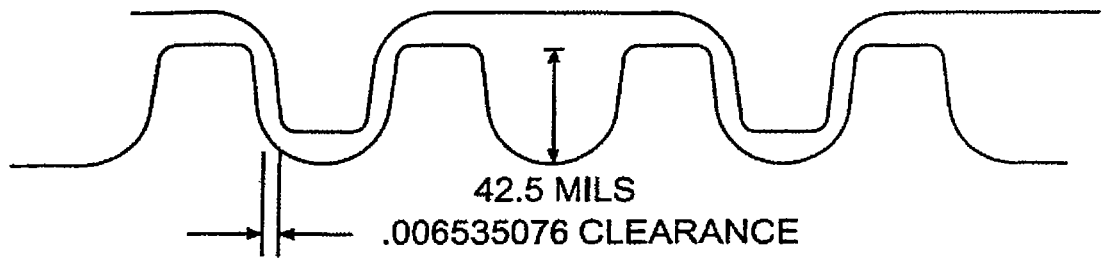
FIGS. 13A-C are side views of the cross-machine direction elements of embodiments of the present invention having differing wall angles and illustrating the effect of the differing wall angles.
Figure 13B:
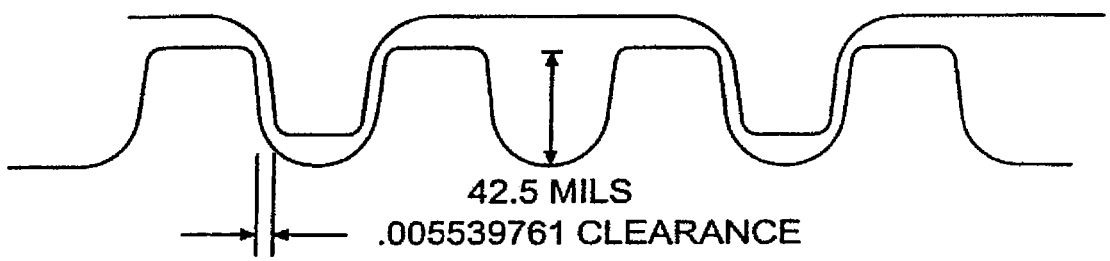
Figure 13C:
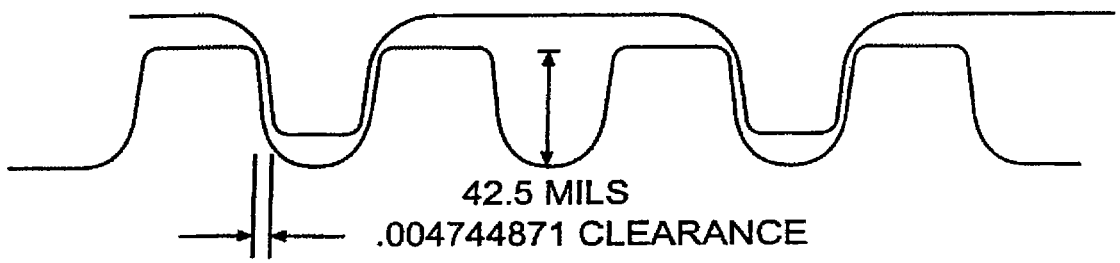
Figure 14A:
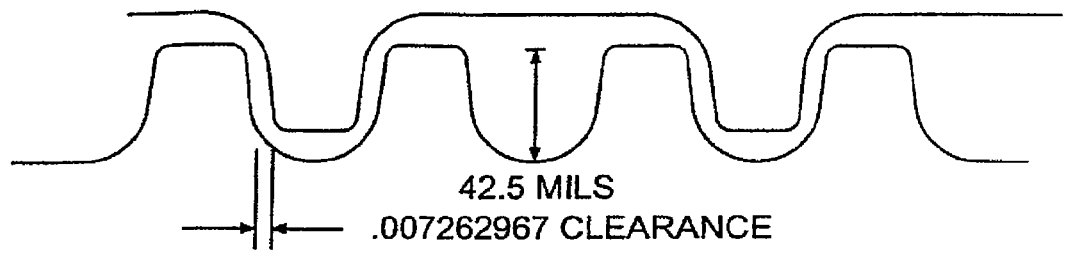
FIGS. 14A-C are side views of the cross-machine direction elements of yet another embodiment of the present invention having differing wall angles and illustrating the effect of the differing wall angles.
Figure 14B:
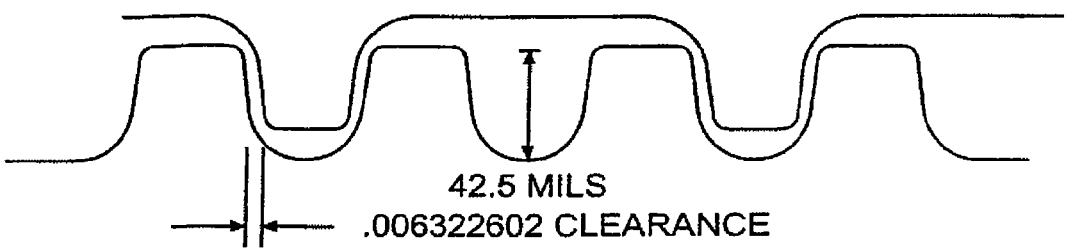
Figure 14C:
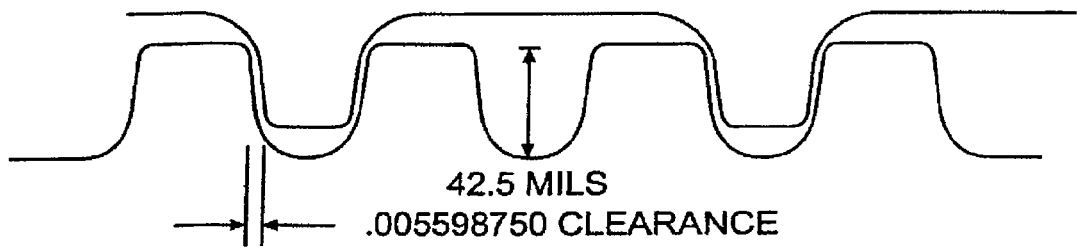

In one embodiment, the engagement is at least about 15 mils. Various engagements are depicted in FIGS. 12-14. In particular, FIG. 12 depicts a 32 mil engagement. That is, the overlap of the elements, in the z-direction, is 32 mils. The desired engagement is determined by a variety of factors, including element height, element sidewall angle, element spacing, desired effect of the embossing elements on the base sheet, and the base sheet properties, e.g., basis weight, caliper, strength, and stretch. Those of ordinary skill in the art will understand that a variety of engagements can be employed based on the above, as well as other factors. It is preferred that the engagement be chosen to substantially degrade the machine direction tensile strength of the web. It is further preferred that the engagement be at least about 5 mils.

In one embodiment, where the element height is about 42.5 mils and the elements have sidewall angles of from about 7° to 11°, the engagement range can be from about 16 to 32 mils. FIG. 12 depicts a 32 mil engagement, where the element heights are 42.5 mils and the sidewall angles are 7°, 9°, and 11°. It is believed that lower sidewall angles make the process significantly easier to run with more controllability and decreased tendency to "picking."

Figure 4:
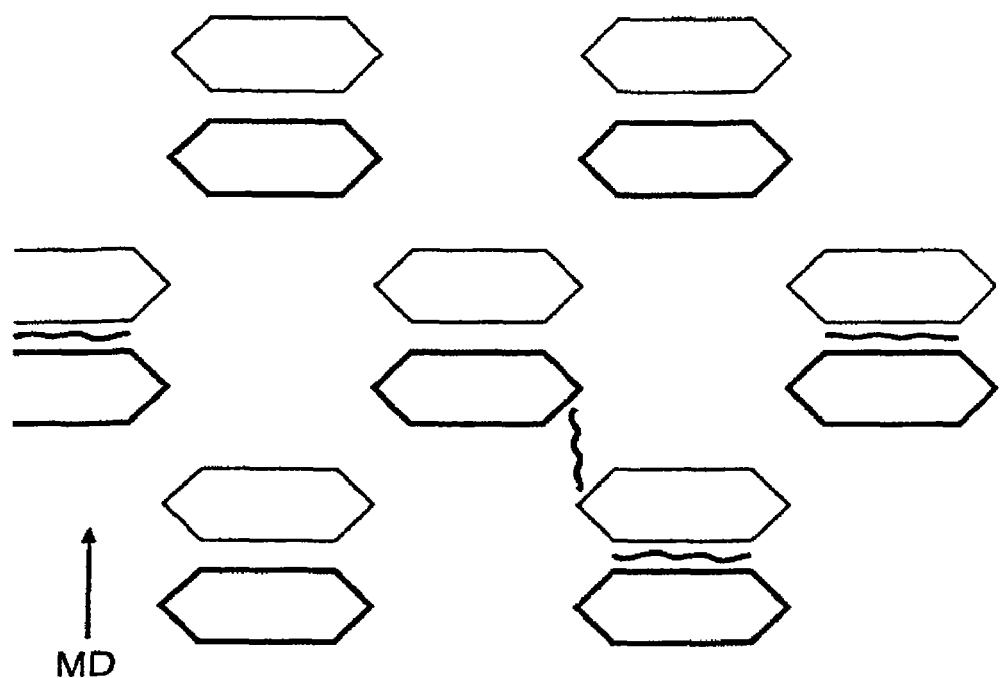
FIG. 4 illustrates the alignment of the cross-machine direction elements according to an embodiment of the present invention.
Figure 5:
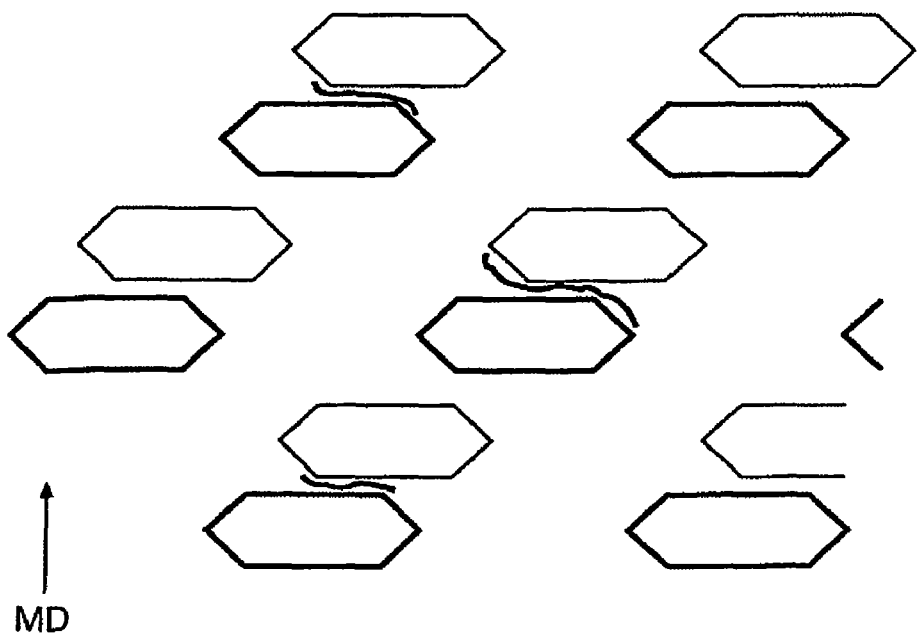
FIG. 5 illustrates the alignment of the cross-machine direction elements according to another embodiment of the present invention.
Figure 6:
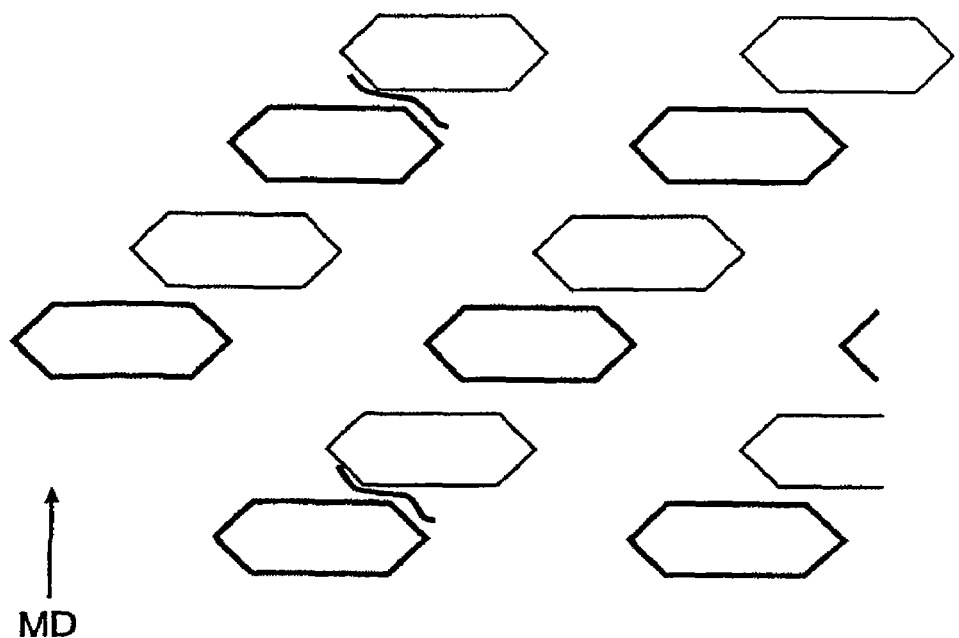
FIG. 6 illustrates the alignment of the cross-machine direction elements according to another embodiment of the present invention.
Figure 7:
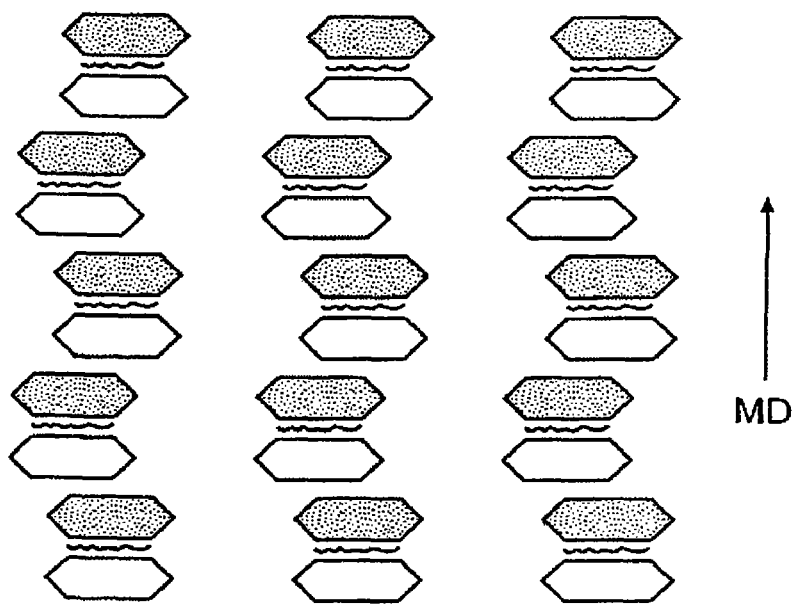
FIG. 7 illustrates the alignment of the cross-machine direction elements according to yet another embodiment of the present invention.

The element alignment also affects the degradation of the web in the machine and cross-machine directions. Element alignment refers to the alignment in the cross-machine direction within the embossing element pairs when the embossing rolls are engaged. FIG. 4 depicts an embodiment including hexagonal embossing elements having a full step alignment, i.e., where the elements are completely overlapped in the cross-machine direction. FIG. 5. depicts an embodiment wherein hexagonal embossing elements are in half step alignment, i.e., where the elements of each element pair are staggered so that half of the engaged portion of their cross-machine direction dimensions overlap. FIG. 6. depicts an embodiment wherein hexagonal embossing elements are in quarter step alignment, i.e., where the elements of each element pair are staggered so that one quarter of the engaged portion of their cross-machine direction dimensions overlap. The embodiment depicted in FIG. 7 is a staggered array, wherein each element pair is in half step alignment with adjacent element pairs. Those of ordinary skill in the art will understand that a variety of element alignments are available for use with this invention, depending upon preferred embossing patterns, web strength requirements, and other factors.

Figure 8:
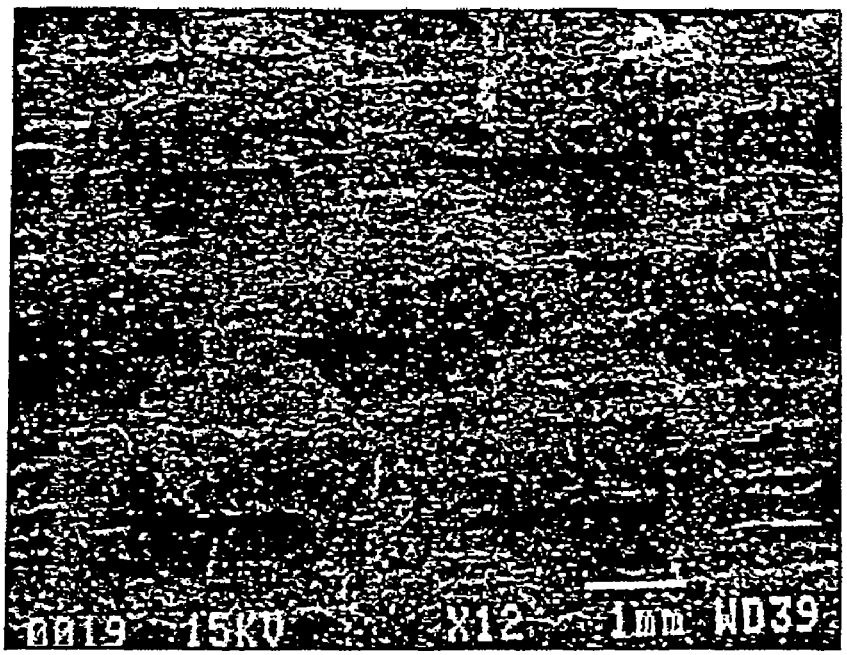
FIG. 8 is a photomicrograph illustrating the effect of cross-machine direction elements on a web according to an embodiment of the present invention.
Figure 9:
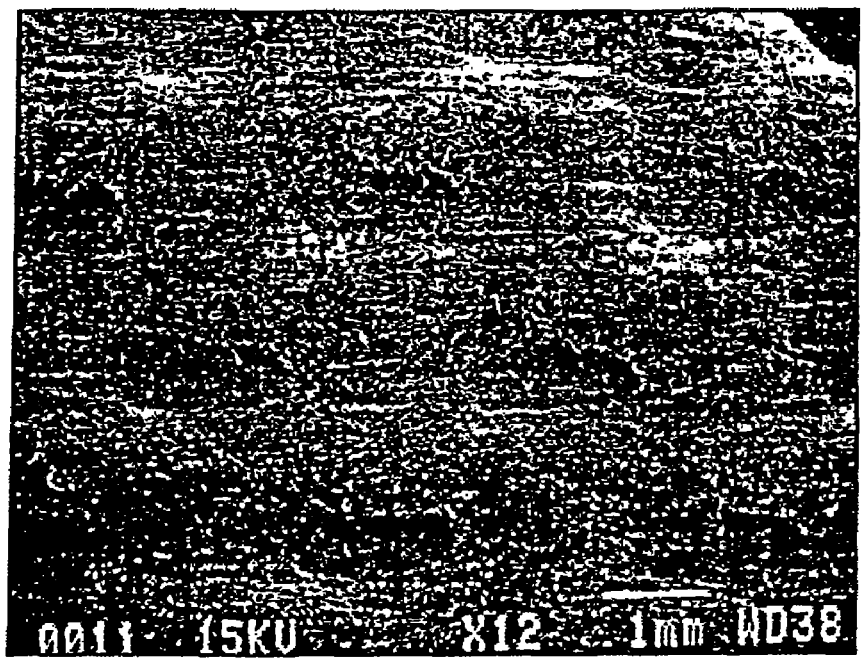
FIG. 9 is a photomicrograph illustrating the effect of cross-machine direction elements on a web according to another embodiment of the present invention.

FIGS. 8-9 depict the effects of various alignments of a hexagonal element arrangement on a web. In the example depicted in FIG. 8, where the elements are in full step alignment, perforations exist only in the cross-machine direction in the area between the element pairs. However, between the pairs of element pairs, occasional machine direction perforations can be caused in the machine direction. The result is a degradation of strength in both the machine and cross-machine directions. In the example depicted in FIG. 9, the web is embossed by element pairs in half step alignment. In this example, the perforations exist primarily in the cross-machine direction, with some minor perforations caused in the machine-direction. Thus, in FIG. 9, machine direction strength is degraded, and cross-machine direction strength is degraded to a lesser extent.

As noted above, the elements can be both in the machine direction and cross-machine direction. FIG. 16 depicts an emboss roll having cross-machine direction and machine direction hexagonal elements.

Figure 10:
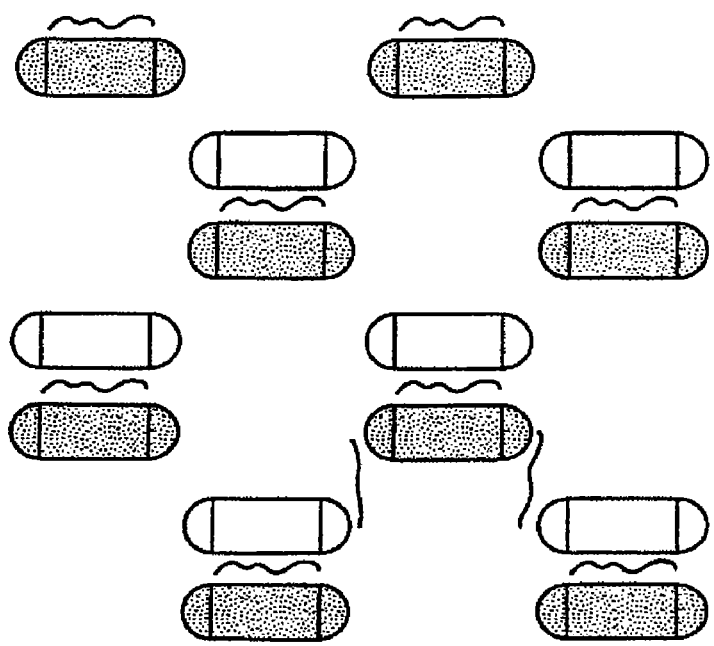
FIG. 10 illustrates the effect of cross-machine direction elements on a web according to yet another embodiment of the present invention.
Figure 11:
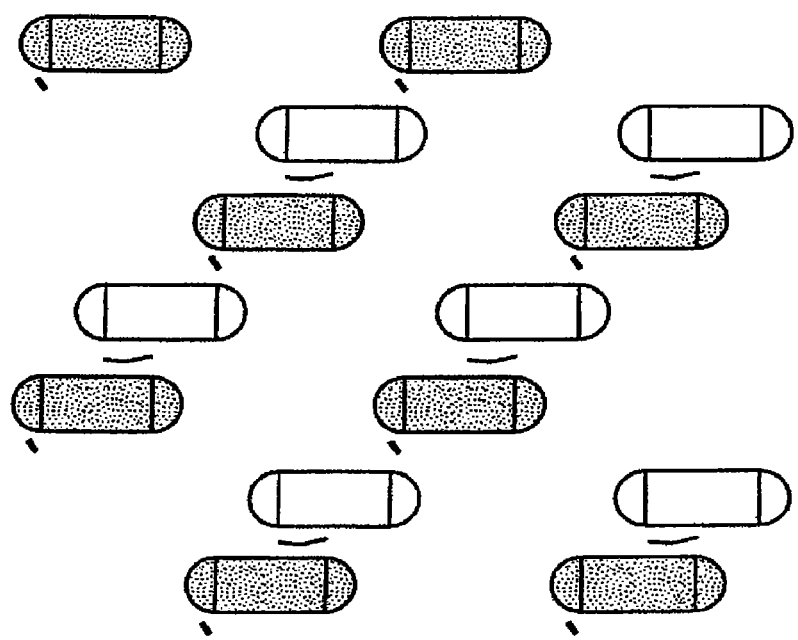
FIG. 11 illustrates the effect of cross-machine direction elements on a web according to yet another embodiment of the present invention.

In another embodiment, depicted in FIG. 10, beveled oval elements are in full step alignment. As with the full step hexagonal elements discussed above, in the area between the element pairs perforations exist primarily in the cross-machine direction. However, between the pairs of element pairs, perforations can be caused in the machine direction. The result is a degradation of strength in both the machine and cross-machine directions. In the embodiment depicted in FIG. 11, on the other hand, where the beveled oval elements in a half step alignment are employed, the machine direction perforations are substantially reduced. In particular, between the elements in half step alignment, the perforation lies primarily in the cross-machine direction. Between the element pairs, which are in zero step alignment, primarily pinpoint ruptures exist. These pinpoint ruptures have a minor effect on degradation of the directional properties of the web.

Those of ordinary skill in the art will understand that numerous different configurations of the above described element parameters, i.e., element shape, angle, sidewall angle, spacing, height, engagement, and alignment, can be employed in the present invention. The selection of each of these parameters may depend upon the base sheet used, the desired end product, or a variety of other factors.

One factor, which is impacted by these parameters, is "picking" of the web as it is embossed. Picking is the occurrence of fiber being left on the embossing roll or rolls as the web is embossed. Fiber on the roll can diminish the runability of the process for embossing the web, thereby interfering with embossing performance. When the performance of the embossing rolls is diminished to the point that the end product is not acceptable or the rolls are being damaged, it is necessary to stop the embossing process so that the embossing rolls can be cleaned. With any embossing process, there is normally a small amount of fiber left on the roll which does not interfere with the process if the roll is inspected periodically, e.g., weekly, and cleaned, if necessary. For purposes of the invention, we define picking as the deposition of fiber on the rolls at a rate that would require shut down for cleaning of the rolls more frequently than once a week.

EXAMPLES

The following examples exhibit the occurrence of picking observed in certain arrangements of cross-machine direction perforate embossed patterns. This data was generated during trials using steel embossing rolls engraved with the cross-machine direction beveled oval embossing pattern at three different sidewall angles. In particular, the embossing rolls were engraved with three separate regions on the rolls—a 7° embossing pattern, a 9° embossing pattern, and an 11° embossing pattern. Two trials were performed. In the first trial, the embossing rolls had an element height of 45 mils. The base sheet, having a thickness of 6.4 mils, was embossed at engagements of 16, 24, and 32 mils. In the second trial, the steel rolls were modified by grinding 2.5 mils off the tops of the embossing elements, thereby reducing the element height to 42.5 mils and increasing the surface area of the element tops. The base sheet having a thickness of 6.2 mils was embossed at engagements of 16, 24, 28, and 32 mils. For each trial, embossing was performed in both half step and full step alignment.

The element clearances for each of the sidewall angles of the first and second trials have been plotted against embossing engagement in FIGS. 19 and 20, respectively. The broken horizontal line on each plot indicates the caliper of a single ply of the base sheet that was embossed. The graphs have been annotated to show whether fiber picking was observed at each of the trial conditions (half step observation being to the left of the slash, full step observation to the right). The picking results are depicted in FIGS. 19 and 20.

FIG. 19 shows that for this particular trial using embossing rolls having a 45 mil element height, picking did not occur at any of the sidewall angles. However, as shown in FIG. 20, when the embossing rolls having a 42.5 mil element height were run, fiber picking was observed on the 11° sidewall angle elements at the higher embossing engagements, i.e., 24, 28, and 32 mils. No fiber picking was encountered with elements having sidewall angles of 7° or 9°.

Based on the observed data, it appears that picking is a function of the element height, engagement, spacing, clearance, sidewall angle, alignment, and the particular physical properties of the base sheet, including base sheet caliper. An example of element clearance can be seen in FIG. 12, where the side profiles of the 42.5 mil elements (having 7°, 9°, and 11° sidewall angles) at 32 mil embossing engagement are shown. Clearance is the distance between adjacent engaging embossing elements. As noted above, the caliper of the embossed sheet for this trial was 6.2 mils. As shown in FIG. 12, the calculated or theoretical clearance at 7° is 0.004906" (4.906 mils), the clearance at 9° is 0.003911" (3.911 mils), and the clearance at 11° is 0.00311" (3.11 mils). Thus, for this trial at a 32 mil engagement, picking was observed only when the clearance was less than about ½ of the caliper of the sheet. Compare this to the clearances shown in FIG. 13. FIG. 13 depicts the sidewall profiles of the 42.5 mil elements at 28 mil embossing engagement. In this arrangement, the calculated or theoretical clearance at 7° is 0.006535" (6.535 mils), the clearance at 9° is 0.005540" (5.540 mils), and the clearance at 11° is 0.004745" (4.745 mils). In this trial, picking was observed when the clearance was less than about ¾ of the caliper of the sheet. Note, however, that when embossing at 32 mils, as described above, picking did not occur at 9°, while the clearance was less than 4.745 mils. FIG. 14 depicts the sidewall profiles of the 42.5 mil elements at 24 mil engagement. In this arrangement, the clearance at 11° is 0.005599" (5.599 mils), slightly less than the caliper of the sheet. As shown on FIG. 20, picking did occur for these elements, but only when the elements were in full step alignment and not when in half step alignment. And, as shown in FIG. 19, picking did not occur at all, at any angle, engagement, or alignment, for the 45 mil embossing rolls.

Thus, based on the collected data, picking can be controlled by varying element height, engagement, spacing, clearance, alignment, sidewall angle, roll condition, and the physical properties of the base sheet. Based upon the exemplified information, those of ordinary skill in the art will understand the effects of the various parameters and will be able to determine the various arrangements that will at least achieve a non-picking operation, i.e., the configuration required to avoid an unacceptable amount of picking based on the factors discussed above, and, hence, produce acceptable paper products with a process that does not require excessive downtime for roll cleaning.

To establish the effectiveness of the various element patterns in perforating the web in the cross-machine direction, and thereby degrading machine direction strength while maintaining cross-machine direction strength, a test was developed, the transluminance test, to quantify a characteristic of perforated embossed webs that is readily observed with the human eye. A perforated embossed web that is positioned over a light source will exhibit pinpoints of light in transmission when viewed at a low angle and from certain directions. The direction from which the sample must be viewed, e.g., machine direction or cross-machine direction, in order to see the light, is dependent upon the orientation of the embossing elements. Machine direction oriented embossing elements tend to generate machine direction ruptures in the web which can be primarily seen when viewing the web in the cross-machine direction. Cross-machine direction oriented embossing elements, on the other hand, tend to generate cross-machine direction ruptures in the web which can be seen primarily when viewing the web in the machine direction.

Figure 15:
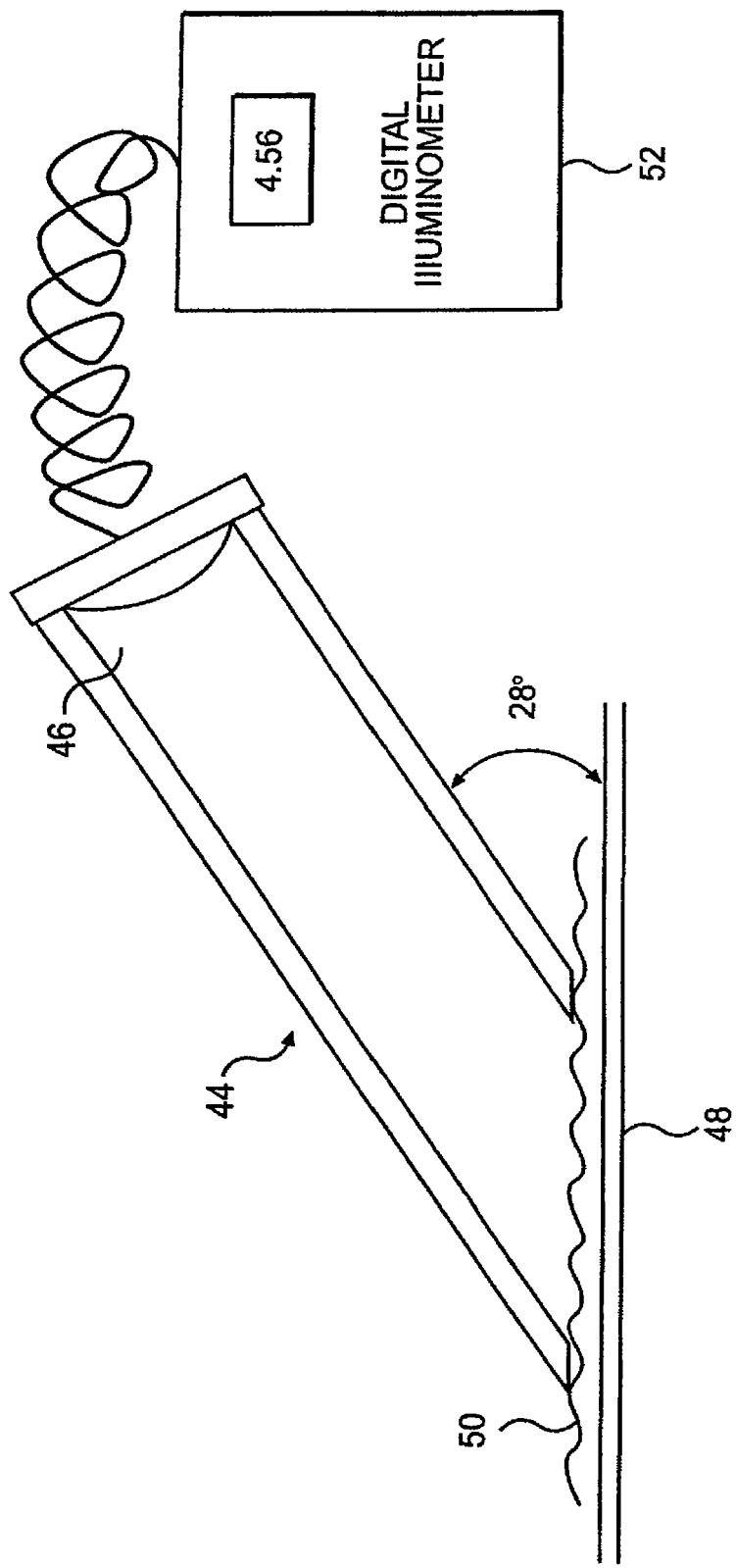
FIG. 15 depicts a transluminance test apparatus.

The transluminance test apparatus, as depicted in FIG. 15, consists of a piece of cylindrical tube 44 that is approximately 8.5" long and cut at a 28° angle. The inside surface of the tube is painted flat black to minimize the reflection noise in the readings. Light transmitted through the web itself, and not through a rupture, is an example of a non-target light source that could contribute to translucency noise which could lead non-perforate embossed webs to have transluminance ratios slightly exceeding 1.0, but typically by no more than about 0.05 points. A detector 46, attached to the non-angled end of the pipe, measures the transluminance of the sample. A light table 48, having a translucent glass surface, is the light source.

The test is performed by placing the sample 50 in the desired orientation on the light table 48. The detector 46 is placed on top of the sample 50 with the long axis of the tube 44 aligned with the axis of the sample 50, either the machine direction or cross-machine direction, that is being measured and the reading on a digital illuminometer 52 is recorded. The sample 50 is turned 90° and the procedure is repeated. This is done two more times until all four views, two in the machine direction and two in the cross-machine direction, are measured. In order to reduce variability, all four measurements are taken on the same area of the sample 50 and the sample 50 is always placed in the same location on the light table 48. To evaluate the transluminance ratio, the two machine direction readings are summed and divided by the sum of the two cross-machine direction readings.

To illustrate the results achieved when perforate embossing with cross-machine direction elements as compared to machine direction elements, a variety of webs were tested according to the above described transluminance test. The results of the test are shown in Table 1.

TABLE 1

Transluminance Ratios

| Basis Weight (lbs/ream) | Creping Method (Blade) | Emboss Alignment | Emboss Pattern | Transluminance Ratio |
|---|---|---|---|---|
| 30 | Undulatory | Full Step | CD Beveled Oval | 1.074 |
| 30 | Undulatory | Half Step | CD Beveled Oval | 1.056 |
| 32 | Undulatory | Half Step | CD Beveled Oval | 1.050 |
| 30 | Undulatory | Half Step | CD Oval | 1.047 |
| 31 | Undulatory | Half Step | CD Oval | 1.044 |
| 31 | Undulatory | Full Step | CD Oval | 1.043 |
| 30 | Undulatory | Full Step | CD Beveled Oval | 1.040 |
| 32 | Undulatory | Half Step | CD Beveled Oval | 1.033 |
| 30 | Undulatory | Half Step | CD Beveled Oval | 1.033 |
| 30 | Undulatory | Full Step | CD Oval | 1.027 |
| 32 | Undulatory | Half Step | CD Beveled Oval | 1.025 |
| 30 | Undulatory | Half Step | CD Oval | 1.022 |
| 31 | Undulatory | Full Step | CD Oval | 1.018 |
| 20 | Undulatory | Half Step | CD Beveled Oval | 1.015 |
| 30 | Undulatory | Half Step | CD Beveled Oval | 1.012 |
| 30 | Undulatory | Full Step | CD Beveled Oval | 1.006 |
| 28 | Standard | Unknown | MD Perforated | 1.000 |
| 24 | Undulatory | Half Step | MD Perforated | 0.988 |
| 22 | Standard | Unknown | MD Perforated | 0.980 |
| 29 | Undulatory | Half Step | MD Perforated | 0.966 |
| 29 | Undulatory | Half Step | MD Perforated | 0.951 |
| 31 | Undulatory | Half Step | MD Perforated | 0.942 |
| 29 | Undulatory | Half Step | MD Perforated | 0.925 |

A transluminance ratio of greater than 1.000 indicates that the majority of the perforations are in the cross-machine direction. For embossing rolls having cross-machine direction elements, the majority of the perforations are in the cross-machine direction. And, for the machine direction perforated webs, the majority of the perforations are in the machine direction. Thus, the transluminance ratio can provide a ready method of indicating the predominant orientation of the perforations in a web.

As noted above, perforated embossing in the cross-machine direction preserves cross-machine direction tensile strength. Thus, based on the desired end product, a web perforate embossed with a cross-machine direction pattern will exhibit one of the following when compared to the same base sheet embossed with a machine direction pattern: (a) a higher cross-machine direction tensile strength at equivalent finished product caliper, or (b) a higher caliper at equivalent finished product cross-machine direction tensile strength.

Furthermore, the tensile ratio (a comparison of the machine direction tensile strength to the cross-machine direction tensile strength—MD strength/CD strength) of the cross-machine perforate embossed web typically will be at or below the tensile ratio of the base sheet, while the tensile ratio of the sheet embossed using prior art machine direction perforate embossing typically will be higher than that of the base sheet. These observations are illustrated by the following examples.

Higher cross-machine direction strength at equivalent caliper is demonstrated in Table 2. This table compares two products perforate embossed from the same base sheet—a 29 pounds per ream (lbs/R), undulatory blade-creped, conventional wet press (CWP) sheet.

TABLE 2

Increased CD Strength at Equivalent Caliper

| Emboss (perforate) | Basis Wt. (lbs/R) | Caliper (mils) | MD Dry Tensile (g/3") | CD Dry Tensile (g/3") | Dry Tensile Ratio (MD/CD) |
|---|---|---|---|---|---|
| CD Hexagonal | 29.1 | 144 | 3511 | 3039 | 1.16 |
| MD Hexagonal | 29.2 | 140 | 4362 | 1688 | 2.58 |

As shown in Table 2, the cross-machine direction perforate embossed web has approximately the same caliper as the machine direction perforate embossed web (144 vs. 140 mils, respectively), but its cross-machine direction dry tensile strength (3039 g/3") is considerably higher than that of the machine direction hexagonal-embossed web (1688 g/3"). In addition, compared to the tensile ratio of the base sheet (1.32), the cross-machine direction perforate embossed web has a lower ratio (1.16), while the machine direction perforate embossed web has a higher ratio (2.58). Thus the method of the present invention provides a convenient, low cost way of "squaring" the sheet—that is, bringing the tensile ratio closer to 1.0.

Higher caliper at equivalent finished product cross-machine direction tensile strength is illustrated by three examples presented in Table 3. For each example a common base sheet (identified above each data set) was perforate embossed with a cross-machine direction and a machine direction oriented pattern (Hollow Diamond is a machine direction oriented perforate emboss).

TABLE 3

Increased Caliper at Equivalent CD Tensile Strength

| Emboss (perforate) | Basis Wt. (lbs/R) | Caliper (mils) | MD Dry Tensile (g/3") | CD Dry Tensile (g/3") | Dry Tensile Ratio (MD/CD) |
|---|---|---|---|---|---|
| Base Sheet—undulatory blade-creped, CWP base sheet with tensile ratio = 1.32 | | | | | |
| CD Quilt | 28.8 | 108 | 4773 | 4068 | 1.17 |
| MD Quilt | 28.8 | 78 | 6448 | 3880 | 1.66 |
| Base Sheet—undulatory blade-creped, CWP base sheet with tensile ratio = 1.32 | | | | | |
| CD Quilt | 29.5 | 154 | 2902 | 2363 | 1.23 |
| MD Quilt | 29.5 | 120 | 5361 | 2410 | 2.22 |
| Base Sheet—undulatory blade-creped, CWP base sheet with tensile ratio = 1.94 | | | | | |
| CD Oval | 24.6 | 75 | 4805 | 2551 | 1.88 |
| Hollow Diamond | 24.1 | 56 | 5365 | 2364 | 2.27 |

In each case, the cross-machine direction perforate embossed product displays enhanced caliper at equivalent cross-machine direction dry tensile strength relative to its machine direction perforate embossed counterpart. Also, the cross-machine direction perforate embossed product has a lower tensile ratio, while the machine direction perforate embossed product a higher tensile ratio, when compared to the corresponding base sheet.

The current invention further allows for a substantial reduction in base paper weight while maintaining the end product performance of a higher basis weight product. As shown below in Table 4, wherein the web is formed of recycled fibers, the lower basis weight cross-machine direction perforate embossed towels achieved similar results to machine direction perforate embossed toweling made with higher basis weights.

TABLE 4

Performance Comparisons.

| | PRODUCT ID | | | |
|---|---|---|---|---|
| | 20204 | 22#30C6 | 30.5#HD | 28#29C8 |
| EMBOSS | Hollow Diamond (MD Perforate) | CD Oval (CD Perforate) | Hollow Diamond (MD Perforate) | CD Oval (CD Perforate) |
| BASIS WT (LBS/REAM) | 24.1 | 22.2 | 31.3 | 28.9 |
| CALIPER | 56 | 62 | 76 | 81 |
| DRY MD TENSILE (g/3") | 5365 | 5057 | 5751 | 4144 |
| DRY CD TENSILE (g/3") | 2364 | 2391 | 3664 | 3254 |
| MD STRETCH (%) | 7.6 | 8.1 | 8.8 | 10.1 |
| CD STRETCH (%) | 6.3 | 6.1 | 5.5 | 5.3 |
| WET MD CURED TENSILE (g/3") | 1236 | 1418 | 1409 | 922 |
| WET CD CURED TENSILE (g/3") | 519 | 597 | 776 | 641 |
| MacBeth 3100 BRIGHTNESS (%) | 72.3 | 72.6 | 73.3 | 73.4 |
| SAT CAPACITY (g/m$^2$) | 98 | 102 | 104 | 119 |
| SINTECH MODULUS | 215 | 163 | 232 | 162 |
| BULK DENSITY | 367 | 405 | 340 | 385 |
| WET RESILIENCY (RATIO) | 0.735 | 0.725 | 0.714 | 0.674 |

In Table 4, two comparisons are shown. In the first comparison, an 24.1 lbs/ream machine direction perforated web is compared with a 22.2 lbs/ream cross-machine direction perforated web. Despite the basis weight difference of 1.9 lbs/ream, most of the web characteristics of the lower basis weight web are comparable to, if not better than, those of the higher basis weight web. For example, the caliper and the bulk density of the cross-machine direction perforated web are each about 10% higher than those of the machine direction perforated web. The wet and dry tensile strengths of the webs are comparable, while the Sintech modulus of the cross-machine direction perforated web (i.e., the tensile stiffness of the web, where a lower number is preferred) is considerably less than that of the machine direction perforated web. In the second comparison, similar results are achieved in the sense that comparable tensile ratios and physicals can be obtained with a lower basis weight web. Paradoxically, consumer data indicates that the 28#29C8 product was rated equivalent to the 30.5#HD product while the 22#30C6 product was at statistical parity with the 20204 product, but was possibly slightly less preferred than the 20204 product.

This invention can be used in a variety of different processes. The webs in each of the above-described examples were formed in a conventional wet press process. However, the invention is equally applicable when the base web is a through air dried web. In addition, to increase the smoothness of the resulting product, the web may be calendered. Or, as in one of the examples above, to increase the bulkiness of the product, an undulatory creping blade such as described in U.S. Pat. No. 5,690,788, which is herein incorporated by reference, may be used. Those of ordinary skill in the art will understand the variety of processes in which the above-described invention can be employed.

It is understood that the invention is not confined to the particular construction and arrangement of parts and the particular processes described herein but embraces such modified forms thereof as come within the scope of the following claims.

What is claimed is:

1. A pair of mated perforate embossing rolls having mated embossing elements, wherein a plurality of the embossing elements are oriented in a substantially cross-machine direction, and wherein said embossing elements are juxtaposed such that the mated elements create at least one perforated embossment.

2. A pair of mated perforate embossing rolls having mated embossing elements, wherein at least a majority of the embossing elements are oriented in a substantially cross-machine direction, and wherein said embossing elements are juxtaposed such that the mated elements create at least one perforated embossment.

3. The perforate embossing rolls of claim 2, wherein the cross-machine embossing elements are in full-step alignment.

4. The perforate embossing rolls of claim 2, wherein the cross-machine embossing elements are in half-step alignment.

5. The perforate embossing rolls of claim 2, wherein the cross-machine embossing elements are in quarter-step alignment.

6. The perforate embossing rolls of claim 2, wherein a portion of the cross-machine embossing elements are in full-step alignment, and wherein a portion of the cross-machine embossing elements are in half-step alignment.

7. The perforate embossing rolls of claim 2, wherein the cross-machine embossing elements are staggered such that pairs of cross-machine embossing elements are in half-step alignment with one another.

8. The perforate embossing rolls of claim 2, wherein the cross-machine embossing elements extend in the cross-machine direction for at least about 10 mils.

9. The perforate embossing rolls of claim 2, wherein the angle between the cross-machine embossing elements and a machine direction is between 60° and 120°.

10. A perforate embossed web formed using the perforate embossing rolls of claim 2, wherein the perforate embossed web has a plurality of cross-machine direction oriented perforations, and wherein the perforate embossed web has a tensile ratio of less than about 1.2.

11. The perforate embossed web of claim 10, further having a transluminance ratio of at least 1.005.

12. The perforate embossed web of claim 10, further having a transluminance ratio of at least 1.01.

13. The perforate embossed web of claim 10, further having a transluminance ratio of at least 1.015.

14. The perforate embossed web of claim 10, further having a transluminance ratio of at least 1.02.

15. The perforate embossed web of claim 10, further having a transluminance ratio of at least 1.025.

16. The perforate embossing rolls of claim 2, wherein the angle between the cross-machine embossing elements and a machine direction is between 45° and 135°.

17. The perforate embossing rolls of claim 2, wherein the angle between the cross-machine embossing elements and a machine direction is between 75° and 105°.

18. The perforate embossing rolls of claim 2, wherein the angle between the cross-machine embossing elements and a machine direction is between 80° and 100°.

19. The perforate embossing rolls of claim 2, wherein the angle between the cross-machine embossing elements and a machine direction is between 85° and 95°.

20. The perforate embossing rolls of claim 2, wherein at least a portion of the embossing elements are male elements.

21. The perforate embossing rolls of claim 2, wherein at least a portion of the embossing elements have a ratio of cross-machine-direction length to machine-direction width greater than 1.0.

22. The perforate embossing rolls of claim 2, wherein at least a portion of the embossing elements have a ratio of cross-machine-direction length to machine-direction width greater than 2.0.

23. The perforate embossing rolls of claim 2, wherein at least a portion of the embossing elements are configured to produce perforating nips extending in the cross-machine direction.

* * * * *